(12) United States Patent
Casagrande et al.

(10) Patent No.: US 7,285,412 B2
(45) Date of Patent: Oct. 23, 2007

(54) DEVICE FOR MAGNETIC IMMOBILIZATION OF CELLS

(75) Inventors: Rocco Casagrande, Newton, MA (US); Evelyn Wang, Haddonfield, NJ (US); Gregory Kirk, Winchester, MA (US); Michael Nussbaum, Newton, MA (US); Enoch Kim, Boston, MA (US); Aaron Raphel, Somerville, MA (US)

(73) Assignee: Surface Logix Inc., Brighton, MA (US)

(*) Notice: Subject to any disclaimer, the term of this patent is extended or adjusted under 35 U.S.C. 154(b) by 327 days.

(21) Appl. No.: 10/084,063

(22) Filed: Feb. 28, 2002

(65) Prior Publication Data

US 2003/0022370 A1 Jan. 30, 2003

Related U.S. Application Data

(60) Provisional application No. 60/334,593, filed on Dec. 3, 2001, provisional application No. 60/307,843, filed on Jul. 27, 2001.

(51) Int. Cl.
| | |
|---|---|
| C12M 1/12 | (2006.01) |
| C12M 1/34 | (2006.01) |
| C12N 11/02 | (2006.01) |
| C12N 11/08 | (2006.01) |

(52) U.S. Cl. .................. 435/297.1; 435/177; 435/180; 435/287.1; 435/287.2

(58) Field of Classification Search .............. 435/4, 435/174, 177, 180
See application file for complete search history.

(56) References Cited

U.S. PATENT DOCUMENTS

| | | | |
|---|---|---|---|
| 4,230,685 A | 10/1980 | Senyei et al. | |
| 4,508,625 A | 4/1985 | Graham | |
| 4,582,622 A | 4/1986 | Ikeda et al. | |
| 4,591,570 A | 5/1986 | Chang | |
| 4,672,040 A | 6/1987 | Josephson | |
| 4,748,124 A | 5/1988 | Vogler | |
| 4,777,145 A | 10/1988 | Luotola et al. | |
| 4,910,148 A | 3/1990 | Sorensen et al. | |
| 4,988,618 A | 1/1991 | Li et al. | |
| 4,992,377 A | 2/1991 | Saxholm | |
| 5,186,827 A | 2/1993 | Liberti et al. | |
| 5,200,084 A | 4/1993 | Liberti et al. | |
| 5,202,227 A | 4/1993 | Matsuda et al. | |
| 5,278,063 A | 1/1994 | Hubbell et al. | |
| 5,330,911 A | 7/1994 | Hubbell et al. | |
| 5,395,498 A | 3/1995 | Gombinsky et al. | |
| 5,427,663 A | 6/1995 | Austin et al. | |
| 5,466,574 A | 11/1995 | Liberti et al. | |
| 5,476,796 A | 12/1995 | Takahashi et al. | |
| 5,486,457 A | 1/1996 | Butler et al. | |
| 5,498,392 A | 3/1996 | Wilding et al. | |
| 5,498,550 A | 3/1996 | Fujiwara et al. | |
| 5,508,164 A | 4/1996 | Kausch et al. | |
| 5,514,340 A | 5/1996 | Landsdorp et al. | |
| 5,567,326 A | 10/1996 | Ekenberg et al. | |
| 5,573,942 A | 11/1996 | Miyamoto | |
| 5,591,627 A | 1/1997 | Miyamoto | |
| 5,593,838 A | 1/1997 | Zanzucchi et al. | |
| 5,602,028 A | 2/1997 | Minchinton | |
| 5,602,042 A | 2/1997 | Farber | |
| 5,612,188 A | 3/1997 | Shuler et al. | |
| 5,646,001 A | 7/1997 | Terstappen et al. | |
| 5,660,990 A | 8/1997 | Rao et al. | |
| 5,665,582 A | 9/1997 | Kausch et al. | |
| 5,681,484 A | 10/1997 | Zanzucchi et al. | |
| 5,755,942 A | 5/1998 | Zanzucchi et al. | |
| 5,759,793 A | 6/1998 | Schwartz et al. | |
| 5,763,203 A | 6/1998 | Ugelstad et al. | |
| 5,776,748 A | 7/1998 | Singhvi et al. | |
| 5,795,470 A | 8/1998 | Wang et al. | |
| 5,812,419 A | 9/1998 | Chupp et al. | |
| 5,858,804 A | 1/1999 | Zanzucchi et al. | |

(Continued)

FOREIGN PATENT DOCUMENTS

| | | |
|---|---|---|
| EP | 0 390 634 B1 | 5/1995 |
| JP | 63-116175 | 5/1988 |
| WO | WO 92/08133 | 5/1992 |
| WO | WO 94/11078 | 5/1994 |

(Continued)

OTHER PUBLICATIONS

Castelino J., "Magnetic Activated Cell Sorting using Microfabricated Arrays", Biomedical Physics (1999), Session Z13. 001 (abstract).
Delamarche E. et al., "Microfluidic Networks for Chemical Patterning of Substrates: Design and Application to Bioassays", J. Am. Chem. Soc. (1998) 120:500-508.

(Continued)

Primary Examiner—David M. Naff
(74) Attorney, Agent, or Firm—Kenyon & Kenyon LLP

(57) ABSTRACT

The present invention relates to an apparatus and methods that immobilize one or more cells associated with magnetic material on a substrate on which are located one or more magnetic receptacle(s). Alternatively, in another aspect the present invention, the device arrays cells associated with magnetic material on a substrate having a pattern of magnetic receptacles disposed thereon. The size of the magnetic receptacle(s) determines the number of target cells that it is capable of immobilizing. The size of the magnetic receptacle is defined by the strength of a localized magnetic field gradient. The localized magnetic field gradient maybe derived from 1) permanent magnets embedded in the substrate or alternatively, the localized magnetic field gradient may be derived from an 2) external magnet whose strength is focused by objects of highly-permeable-magnetic material which create localized magnetic field gradients. The invention apparatus comprises a removable cell delivery device and a substrate, which has one or more magnetic receptacles disposed thereon.

16 Claims, 7 Drawing Sheets

U.S. PATENT DOCUMENTS

| | | | |
|---|---|---|---|
| 5,876,593 | A | 3/1999 | Liberti et al. |
| 5,912,177 | A | 6/1999 | Turner et al. |
| 5,922,284 | A | 7/1999 | Kinoshita et al. |
| 5,928,880 | A | 7/1999 | Wilding et al. |
| 5,968,820 | A | 10/1999 | Zborowski et al. |
| 5,972,721 | A | 10/1999 | Bruno et al. |
| 5,989,835 | A | 11/1999 | Dunlay et al. |
| 5,993,665 | A | 11/1999 | Terstappen et al. |
| 5,993,740 | A | 11/1999 | Niiyama et al. |
| 5,998,160 | A | 12/1999 | Berens |
| 5,998,224 | A | 12/1999 | Rohr et al. |
| 6,008,010 | A | 12/1999 | Greenberger et al. |
| 6,013,188 | A | 1/2000 | Terstappen et al. |
| 6,013,532 | A | 1/2000 | Liberti et al. |
| 6,027,945 | A | 2/2000 | Smith et al. |
| 6,039,897 | A | 3/2000 | Lochhead et al. |
| 6,090,251 | A | 7/2000 | Sundberg et al. |
| 6,110,380 | A | 8/2000 | Barbera-Guillem |
| 6,126,835 | A | 10/2000 | Barbera-Guillem et al. |
| 6,133,043 | A | 10/2000 | Talley et al. |
| 6,136,182 | A | 10/2000 | Dolan et al. |
| 6,140,045 | A | 10/2000 | Wohlstadter et al. |
| 6,143,247 | A | 11/2000 | Sheppard, Jr. et al. |
| 6,180,239 | B1 | 1/2001 | Whitesides et al. |
| 6,180,418 | B1 | 1/2001 | Lee |
| 6,184,043 | B1 | 2/2001 | Fodstad et al. |
| 6,187,214 | B1 | 2/2001 | Gañán-Calvo |
| 6,221,663 | B1 | 4/2001 | Bhatia et al. |
| 6,235,541 | B1 | 5/2001 | Brizzolara |
| 6,238,538 | B1 | 5/2001 | Parce et al. |
| 6,258,607 | B1 | 7/2001 | Saito et al. |
| 6,558,904 | B2 | 5/2003 | Ermantraut et al. |
| 2002/0012953 | A1 | 1/2002 | Jauho et al. |
| 2002/0022276 | A1 | 2/2002 | Zhou et al. |

FOREIGN PATENT DOCUMENTS

| | | |
|---|---|---|
| WO | WO 97/28490 | 8/1997 |
| WO | WO 99/42832 | 8/1999 |
| WO | WO 00/43783 | 7/2000 |
| WO | WO 00/54882 | 9/2000 |
| WO | WO 00/60356 | 10/2000 |
| WO | WO 01/51668 | 7/2001 |

OTHER PUBLICATIONS

Delamarche E. et al., "*Patterned Delivery of Immunoglobulins to Surfaces Using Microfluidic Networks*", Science (1997) 276:779-781.

Fishman D. et al., "*Biological Assays in Microfabricated Structures*", SPIE (1999) 3603:192-197.

Folch A. et al., "*Microengineering of Cellular Interactions*", Annu. Rev. Biomed. Eng. (2000) 2:227-256.

Love J.C. et al., "*Fabrication of Three-Dimensional Microfluidic Systems by Soft Lithography*", MRS BULLETIN (2001) 523-528.

Quake S.R. et al., "From Micro- to Nanofabrication with Soft Materials", Science (2000) 290:1536-1540.

Šafařík I. et al., "Use of magnetic techniques for the isolation of cells", Journal of Chromatography B. (1999) 722:33-53.

Bhatia et al., "Selective Adhesion of Hepatocytes on Patterned Surfaces," Annals New York Academy of Sciences, 745:187-209 (1994).

Blawas et al., "Protein Patterning," Biomaterials, 19:595-609 (1998).

Britland et al., "Micropatterning Proteins and Synthetic Peptides on Solid Supports: A Novel Application for Microelectronics Fabrication Technology," Biotechnol. Prog., 8(2):155-160 (1992).

Chen et al., "Using Self-Assembled Monolayers to Pattern ECM Proteins and Cells on Substrates," Methods in Molecular Biology-Extracellular, Matrix Protocols, 139:209-219 (2000).

Chiu et al., "Patterned Deposition of Cells and Proteins Onto Surfaces by Using Three-Dimensional Microfluidic Systems," PNAS, 97(6): 2408-2413 (2000).

Dasgupta et al., "Visualizing Thin-Layer, 2-D Flow and Chemical Interaction Can be Done Simply and Cheaply," Analytical Chemistry, 74(7):209A-213A (2002).

Hodneland et al., "Selective Immobilization of Proteins to Self-Assembled Manolayers Presenting Active Site Directed Capture Ligands," PNAS, 99(8): 5048-5052 (2002).

Jung et al., "Topographical and Physicochemical Modification of Material Surface to Enable Patterning of Living Cells," Critical Reviews in Biotechnology, 21(2): 111-154 (2001).

Saleemuddin, "Bioaffinity Based Immobilization of Enzymes," Advances in Biochemical Engineering/Biotechnology, 64:203-226 (1999).

International Search Report, International Application No. PCT/US03/05841, dated Jan. 26, 2007 (6 pages).

DEVICE FOR MAGNETIC IMMOBILIZATION OF CELLS

CROSS-REFERENCE TO RELATED APPLICATIONS

This application claims the benefit of U.S. Provisional Application No. 60/334,593, filed Dec. 3, 2001, and U.S. Provisional Application No. 60/307,843, filed Jul. 27, 2001.

FIELD OF THE INVENTION

The present invention relates to methods and devices that are useful in immobilizing, arraying and/or isolating cells individually. In particular, the present invention relates to methods and devices that are useful for immobilizing, arraying and/or isolating cells using a magnetic source.

BACKGROUND OF THE INVENTION

Many biological techniques employed in biotechnology, microbiology, clinical diagnostics and treatment, in vitro fertilization, hematology and pathology, require such processes as identification, separation, culturing, immobilization and/or manipulation of a target entity. Typical target entities include cells or microbes within a fluid medium such as culture fluids, environmental samples, blood or other bodily fluids. It is often desirable to retain viability of the target entity or to culture the target entity. When screening individual cells in a heterogenous population, it is desirable to array cells at discrete and separable locations. For example, an array of genotypically or phenotypically diverse cells would allow the investigator to rapidly perform large numbers of automated assays and observe results at the single cell level. The cell of interest could then also be further isolated and clonally expanded.

Isolation techniques typically involve labeling the target entity with a reagent that can be selected according to a characteristic property. Entities such as eukaryotic cells or certain microbes may be sorted using fluorescence-labeled monoclonal antibodies (Mabs) that are specific to a particular class of cells or microbes. Fluorescence Activated Cells Sorting (FACS) allows cells to be separated into different pools based on their reactivity to specific fluorescent Mabs. However, sorting cells into pools does not allow the investigator to experiment on or manipulate individual cells.

Manipulation of individual target cells required by certain biological techniques may involve such processes as insertion of genetic material, subcellular components, viruses, or other foreign materials or bodies into the target entities. In techniques such as transfection, cell injection or in vitro fertilization, mechanical probes or arms are often used to hold target cells in place. Such mechanical holding methods tend to obscure or damage the target cells. Experiments on isolated and immobilized individual cells also include hybridoma screening, patch-clamp experiments, single cell PCR and the like.

Devices and methods for precise non-destructive immobilization of specific individual target entities in an array of discrete locations, especially in an inexpensive and rapid manner are desirable.

Magnetic-based systems are commonly used to isolate and immobilize cells and rely on the use of cell-binding magnetic beads and a mechanism for cell capture. Although current magnetic-based cell separation methods afford certain advantages in performing medical or biological analyses based on biospecific affinity reactions involving colloidal magnetic particles, the systems developed to date are not particularly suited for immobilization or micromanipulation of individual cells.

A currently used method to isolate and immobilize cells involves placing steel wool inside a collecting vessel and then placing the vessel inside a strong magnetic field. A cell-containing fluid is mixed with magnetic beads that can specifically or non-specifically bind cells. The magnetic beads are generally coated with an antibody or compound that non-specifically binds cells. An operator pours the cell-containing fluid mixture through a magnetically activated cell sorting (MACS) magnetic filter that collects cells bound to magnetic particles. For example, a MACS device made by Miltenyi Biotec GmbH, Gladbach, Germany, employs a column filled with a non-rigid steel wool matrix in cooperation with a permanent magnet. In operation, the enhanced magnetic field gradient produced in the vicinity of the steel wool matrix attracts and retains the magnetic particles, while the non-magnetic components of the test medium pass through the column. It has been found that the steel wool matrix of such prior art high-gradient magnetic separation (HGMS) devices often causes non-specific entrapment of biological entities other than target entities. The entrapped non-magnetic components cannot be removed completely without extensive washing and resuspension of the particles bearing the target substance. Moreover, sizes of the columns in many of the prior art HGMS devices require substantial volumes of test media, which poses an impediment to their use in performing various laboratory-scale separations. In addition, the steel wool matrix may damage sensitive cell types. Furthermore, immobilizing target cells on steel wool does not allow the investigator to experiment on or manipulate individual target cells.

Another method for magnetically sorting and isolating cells has been to place bent metal pins inside microtiter wells and then move the holder for the microtiter wells inside a strong magnetic field. In the presence of the enhanced magnetic gradients, cells decorated with magnetic beads can be captured from any fluid samples inside the vessel or microtiter wells onto the bent metal pins. After the magnetic fields are removed, the captured magnetic beads can be removed from the bent pins by various techniques. This technique is primarily a batch process. As above, immobilizing target cells on bent metal pins does not allow the investigator to immobilize, array and/or isolate individual target cells.

Magnetic-based isolators are also used to purify nucleic acid or proteins from mixed samples, however, none can immobilize, array and/or isolate cells for study. Those magnetic-based cell isolators are intended to purify certain types of cells or molecules away from a background of other cells or molecules, respectively.

Thus, it is seen that there is a need for a magnetic-based system that can rapidly and efficiently immobilize, array and/or isolate target cells associated with magnetic particles from fluid samples on a substrate.

SUMMARY OF THE INVENTION

The invention provides for a device for immobilizing cells associated with magnetic material in a cell-containing fluid comprising a substrate having one or more magnetic receptacle(s), and a cell delivery device; wherein the magnetic receptacle comprises a permanent magnet and a localized magnetic field gradient.

The invention also provides for a device for immobilizing cells associated with magnetic material in a cell-containing fluid comprising a substrate having one or more magnetic receptacle(s), an external magnetic field and a cell delivery device; wherein the magnetic receptacle comprises highly-magnetically-permeable material and a localized magnetic field gradient.

The invention further provides for a device for arraying cells associated with magnetic material in a cell-containing fluid comprising a substrate having magnetic receptacles, arrayed in a discrete pattern, and a cell delivery device; wherein the magnetic receptacle comprises a permanent magnet and a localized magnetic field gradient.

The invention also provides for a device for arraying cells associated with magnetic material in a cell-containing fluid comprising a substrate having magnetic receptacles, arrayed in discrete patterns, an external magnetic field and a cell delivery device; wherein the magnetic receptacle comprises highly-magnetically-permeable material and a localized magnetic field gradient.

The invention also provides for a method of arraying cells on a substrate in a discrete pattern comprising; providing a cell-containing solution; associating cells in the cell-containing solution with magnetic material using a bioaffinity ligand, delivering the cells associated with magnetic material to a substrate having magnetic receptacles disposed thereon, each magnetic receptacle trapping from about one to about five of said cells associated with magnetic material on the substrate and washing the substrate with a cell-free solution, to form an array of cells thereon.

The invention further provides for a method of arraying about one to about five cells into a discrete location for further experimentation comprising, associating the cells with magnetic beads to yield magnetically associated cells using a bioaffinity ligand, delivering the magnetically associated cells to a substrate having magnetic receptacles, comprising a localized magnetic field gradient, disposed in a two-dimensional array thereon such that about one to about five the magnetically associated cells are immobilized in each of said having magnetic receptacles.

The invention also provides for device for arraying about one to about five cells into a discrete location for further experimentation comprising a substrate having magnetic receptacles, comprising a localized magnetic field gradient, disposed in a two-dimensional array thereon such that about one to about five cells associated with magnetic beads are immobilized in each of the magnetic receptacles.

DESCRIPTION OF THE DRAWINGS

In FIG. 5A, the cell isolation device is a micro through-hole containing membrane which may have an additional membrane 553 opposite the substrate 510 restricting cell 530 movement. The cell isolation device is mated to the substrate 510. B) Alternatively the cell isolation device 550 may also include a membrane having inverted wells 554, rather than through-holes, with a periodicity matching the array of magnetic receptacles 511 on the substrate 510. The interface between the cell isolation device having a membrane with inverted wells 554 and the substrate 510 on which cells are immobilized seals the inverted well and completely encapsulates cells into discrete chambers. A semi-permeable membrane may be fabricated to facilitate medium exchange 555 while restraining cells 530. C) A mechanism for transferring cells 530 from the substrate 510 to the cell isolation device 554. This mechanism for transferring cells from their magnetic receptacles 511 to the inverted membrane wells of the cell isolation device 554 is intended to function by use of centrifugal force. Cells immobilized on the substrate 510 can be spun into the larger membrane well 554 of the cell isolation device. The cell isolation device 554 and substrate 510 are inverted, i.e. turned upside down, and the substrate 510 removed. Removal of the inverted substrate 510 brings the cell isolation device 554 to right-side-up conformation resembling a membrane with a plurality of wells 556, similar to a microtiter plate, with a periodicity matching that of the magnetic receptacles 511 of the substrate 510. Cells are thus transferred into the right-side up wells of the cell isolation device 556. The cell isolation device wells 554 maintain the same periodicity as the substrate. A cell delivery device 550 wherein the well containing membrane may have a semipermeable opening 555 (shown in FIG. 4B) at the opposite the substrate 510 of each inverted well 554 restricting cell movement, yet permitting exchange of media.

DETAILED DESCRIPTION OF THE INVENTION

Figure 1:
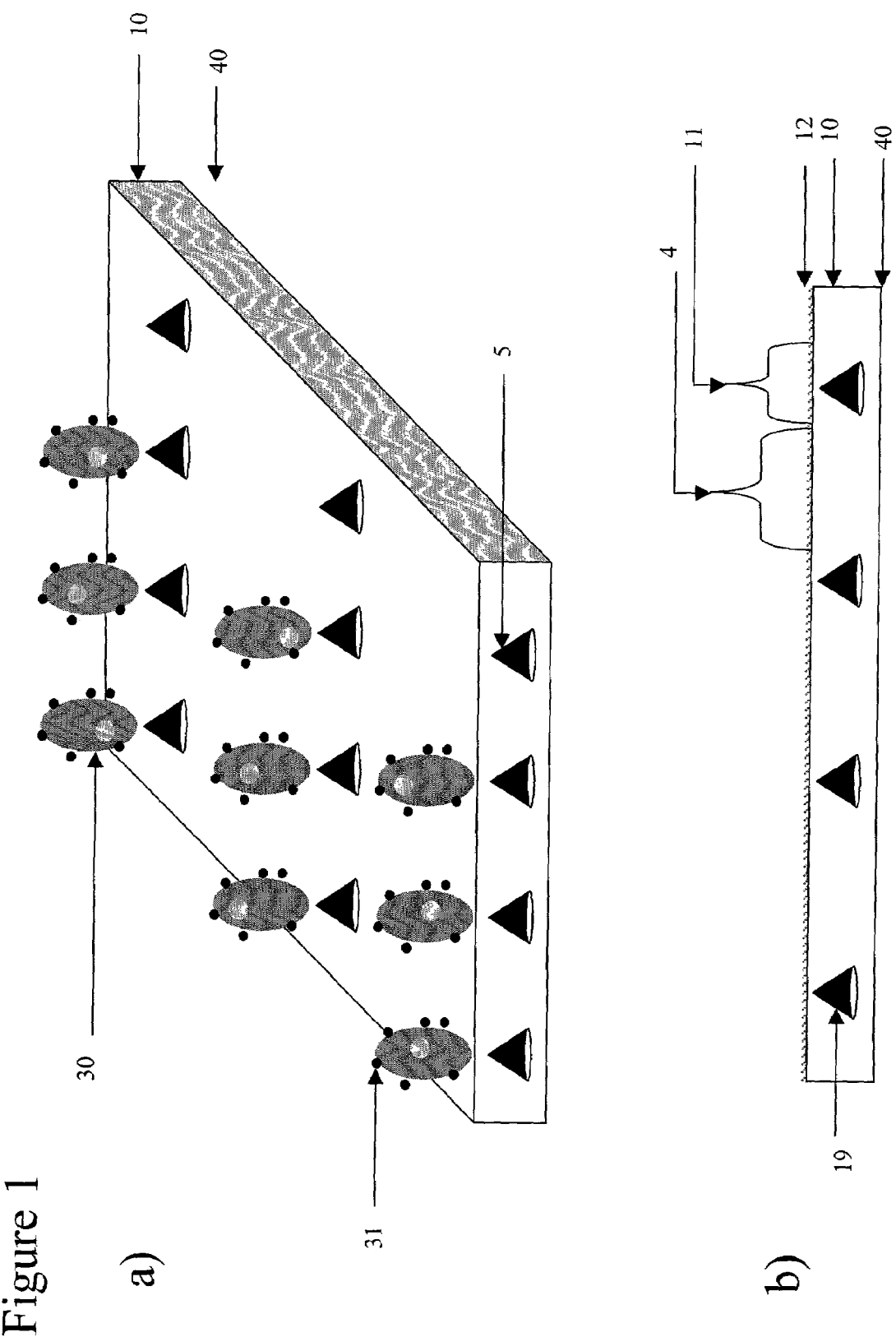
FIG. 1A) shows the substrate 10 in which are embedded permanent magnets 5 which arrest cells 30 associated with magnetic material 31, in a perspective view. B) Illustrates in a cross-sectional view, permanent magnetic horns 19 embedded in the substrate 10 to define a magnetic receptacle 11. The substrate may be treated to facilitate beading of cell-containing fluid 12. Area 4 shows an area outside of the magnetic receptacle which is not sufficiently magnetically attractive to immobilize cells associated with magnetic material.

The present invention provides an apparatus and methods that immobilize one or more cells associated with magnetic material on a substrate on which are located one or more magnetic receptacle(s). Alternatively, in another aspect of the present invention, the device arrays cells associated with magnetic material on a substrate having a pattern of magnetic receptacles disposed thereon. The size of the magnetic receptacle(s) determines the number of target cells that it is capable of immobilizing. The size of the magnetic receptacle is defined by the strength of a localized magnetic field gradient. The localized magnetic field gradient may be derived from 1) permanent magnets embedded in the substrate or alternatively, the localized magnetic field gradient may be derived from 2) an external magnet whose strength is focused by objects of highly-permeable-magnetic material which provide a localized magnetic field gradient. The invention apparatus comprises a removable cell delivery device and a substrate, which has one or more magnetic receptacles disposed thereon.

A "cell-containing fluid" is herein defined as any liquid carrier of cells such as all types of cell culture media with or without serum, and also includes blood, plasma, stool, urine, as well as buffered isotonic solutions capable of supporting cell suspensions. A cell-containing solution may also be an environmental sample containing microorganisms from bodies of water such as lakes, ponds, streams or oceans, etc.

"Associating" cells with magnetic material as referred to herein relates to either adhering magnetic material to a cell surface, penetrating magnetic material through the plasma membrane or by having cells phagocytose or pinocytose magnetic material. All of these processes may be facilitated by a bioaffinity ligand. Generally, one is not able to move cells in culture using magnetic force. Associating cells with magnetic material allows cells to be moved from one place to another by way of magnetic attraction or repulsion. Associating cells with magnetic material in the context of this invention, facilitates immobilizing, arraying and/or isolating the cells into one or more magnetic receptacles. Magnetic material is coated and/or conjugated to a bioaffinity ligand which mediates association of magnetic material with the cells. Binding magnetic material to the surface of a cell is also commonly referred to as decorating the cells. However, the invention envisages any method of associating magnetic material with a cell either by binding of magnetic material to the cells' surface, penetration of the cell surface with magnetic material or by pinocytosis or phagocytosis of magnetic material by the cells. Generalized methods of associating cells with magnetic material is described in a review article by Safarik and Safarikova, Journal of Chromatography B, 722:33-53 (1999), which is herein incorporated by reference in its entirety.

"Inherently magnetic" refers to those cells that are inherently associated with magnetic material and that may be immobilized and/or arrayed in the subject invention without an ectopic association with magnetic material from an exogenous source. Such cells do not require experimental association with magnetic material because they are already inherently associated with magnetic material. For example, dimagnetic red blood cells have a high iron content, and can be converted to paramagnetic cells by oxidation of the iron atoms in the cell hemoglobin to the ferric state (methemoglobin). In another example, erythrocytes, infected by *Plasmodium*, containing paramagnetic hemozoin, that is a component of malarial pigment, whose paramagnetic moment is sufficient to separate infected from non-infected erythrocytes. Another example of inherently magnetic cells are magnetotactic bacteria containing small magnetic particles within their cells. Therefore, the technician is able to immobilize, array, and/or isolate these types of cells using the magnetic techniques and devices described herein, without themselves having to associate these particular types of cells with magnetic material.

The term "bioaffinity ligand" is defined herein to mean any biological or other organic molecule capable of specific or nonspecific binding or interaction with another biological molecule (including biological molecules on the surface of cells), which binding or interaction may be referred to as "ligand/ligate" binding or interaction and is exemplified by, but not limited to, antibody/antigen, antibody/hapten, enzyme/substrate, enzyme/inhibitor, enzyme/cofactor, binding protein/substrate, carrier protein/substrate, lectin/carbohydrate, receptor/hormone, nucleic acid/nucleic acid, oligonucleotides/nucleic acid, receptor/effector or repressor/inducer bindings or interactions. Magnetic material may be coated with a bioaffinity ligand to either specifically or non-specifically bind and/or be phagocytosed or pinocytosed by or permeate the plasma membrane of target cells.

Exemplary bioaffinity ligands having a general non-specific affinity to cells are the lanthanides (Ce, atomic no. 58 through lutetium (Lu, atomic no. 71) are commonly known as the lanthanide series). In particular erbium is known to bind cell surface glycoproteins as well as calcium-receptors. Another, bioaffinity ligands having a general non-specific affinity to cells is ferritin.

In another embodiment of this aspect of the invention, the bioaffinity ligand-coated magnetic particle is a magnetic bead coupled to an antibody specific for mammalian cells. For example, anti-Ig kappa light chain antibody, anti-CD45R antibody, or anti-syndican, is used to differentially array activated B-cells. Preferably, an antibody specific for anti-Ig kappa light chain antibody cells is used. Any of the methods known in the art for conjugating an antibody to a solid phase support, such as the magnetizable particle described herein, can be used in this invention. The amount of antibody will depend on the antibody affinity as well as antigen density of the target cell population. Such antibody-coated magnetic beads may be phagocytosed by the cells to which they bind. In another example, cells are pre-incubated with a biotinylated antibody. The cells are then washed to remove excess antibody. The antibody-bound cells are then incubated with the magnetic material conjugated to streptavidin.

In yet a further example, magnetic material is coated, through adsorption or covalent immobilization, with lectins, e.g. *Ulex europaeus* I lectin which binds to the terminal L-fucosyl residues present on the surface of human endothelial cells. Cells immobilized and/or arrayed using lectin can be separated from the magnetic material exposing the cells to free competing sugar. Other suitable lectins include: peanut agglutinin, agglutinin-I, and phytohaem agglutinin.

Alternatively, the "magnetic material" $Fe_2O_3$ may in function as a "bioaffinity ligand". Submicron particles of $Fe_2O_3$ adhere to the cell surfaces of *Saccharomyces cervisiae*, making the cells magnetic and amenable to magnetic separation.

The term "magnetic material", is used herein to mean particles known in the art currently or in the future, which can be used to achieve magnetic separation and/or manipulation of cells by responsiveness and attraction to a magnetic field. Magnetic material envisioned for the current invention is described in a review article by Safarik and Safarikova, Journal of Chromatography B, 722:33-53 (1999), which is herein incorporated by reference in its entirety.

Magnetic materials are contemplated to include biologically active colloidal magnetic materials (ferrofluids). Ferrofluids (Immunicon, Huntington Valley, Pa., USA) are magnetic colloids composed typically of 5-50 nm crystalline magnetic cores (typically magnetite, $Fe_3O_4$) and a surface monolayer coating. Ferrofluids have the following unique properties: (1) they behave as macromolecules, not solid surfaces, with respect to reaction kinetics because they are capable of Brownian motion, (2) they are superparamagnetic, and (3) may be an order of magnitude more sensitive than magnetic beads to a magnetic field gradient.

Additionally, magnetoliposomes which incorporate colloidal magnetic materials into lipid vesicles are contemplated as magnetic materials.

Magnetic materials are also contemplated to include magnetic particles, also known in the art as magnetic spheres, or magnetic beads or microclusters, containing one or more compounds including, but not limited to, a "metal oxide core" containing one or more metals, metal oxides, metal alloys, metal salts, metal organic particles, metal hydroxides, and mixed lattices thereof. The term "metal oxide core" is defined as a crystal or group (or cluster) of crystals of a transition metal oxide having ferrospinel structure and containing trivalent and divalent cations of the same or different transition metals. By way of illustration, a metal oxide core may contain of a cluster of superparamagnetic crystals of an iron oxide, or a cluster of ferromagnetic crystals of an iron oxide, or may contain a single ferromagnetic crystal of an iron oxide. Inorganic cores are also known in the art to include iron, cobalt, nickel, ferric oxide, nickel oxide, cobaltic oxides, or ferrites. Additionally, the magnetic particle may also include a polymeric coating for attachment to biological materials, a biodegradable coating, and/or another functional type of coating that may be useful or advantageous in magnetic separation. Biodegradable coatings on magnetic particles are known to those skilled in the art (for a review, see, e.g., U.S. Pat. Nos. 5,707,877; 5,382,468). Magnetic particles ranging in size from 3 nm to many microns have been described in the patent literature, including, by way of example, U.S. Pat. Nos. 3,970,518; 4,018,886; 4,230,685; 4,267,234; 4,452,773; 4,554,088; 4,659,678; 4,978,610; and 5,200,084. Such small magnetic particles have proved to be particularly useful in analyses involving biospecific affinity reactions. They are readily coated with biofunctional polymers, such as proteins, provide very high surface areas and give reasonable reaction kinetics.

Choice of the magnetic system is dependent on the particles used to target the particular cell population. The beads can be much smaller than the targeted cells, typically about 1 µm to about 30 µm, preferably 5 µm to about 20 µm in diameter, as compared to an about 10 to about 50 µm cell diameter. The ratio of about one to about ten beads per cell to be isolated and arrayed is preferable. Most preferably, a ratio of about four beads per cell is used.

Cells associated with paramagnetic beads that are non-magnetic unless in the presence of a magnetic field, do not aggregate to form magnetically bound colloids. Thus, the beads will not tend to clump together, which would potentially interfere with their interaction with the target species. However, ferromagnetic beads may be substituted, especially if certain precautions are taken. Upon binding to the target cell surface, phagocytosis and/or upon being absorbed through the cell membrane and into the cell, the beads give the selected cells an activatable magnetic property.

Ferromagnetic materials have a net magnetization µ after being magnetized in an applied magnetic field. The material is demagnetized when it is raised above its Curie temperature. Nonporous ferromagnetic beads are also available. Like paramagnetic beads, they may also have surface functional groups that may be used to covalently immobilize receptors. See Wang, N., Butler, J. P., Ingber, D. E. (1993) Science 260, 1124-1127.

If ferromagnetic beads are used, however, they generally should either (1) be kept above their curie temperature until, in situ, one is ready to perform an analysis, or (2) not be magnetized in a magnetizing field until, in situ, one is ready to perform an analysis.

Currently, at least about a dozen companies sell superparamagnetic beads suitable for biological separation, including Bang and Biomag. Commercially available beads with diameters between about 0.2 µm and about 200 µm have surface areas that are large enough to apply high quality uniform coatings, in a manner consistent with the objects of the invention. Such beads typically will experience forces of magnitudes that are likewise consistent with the objects of the invention under reasonable applied fields. Fortunately, such beads are also viewable with the optical microscopes for further manipulation of immobilized cells. This synergism between the beads, the fields, and the preferred optical microscope viewing mechanism is particularly advantageous.

Figure 2:
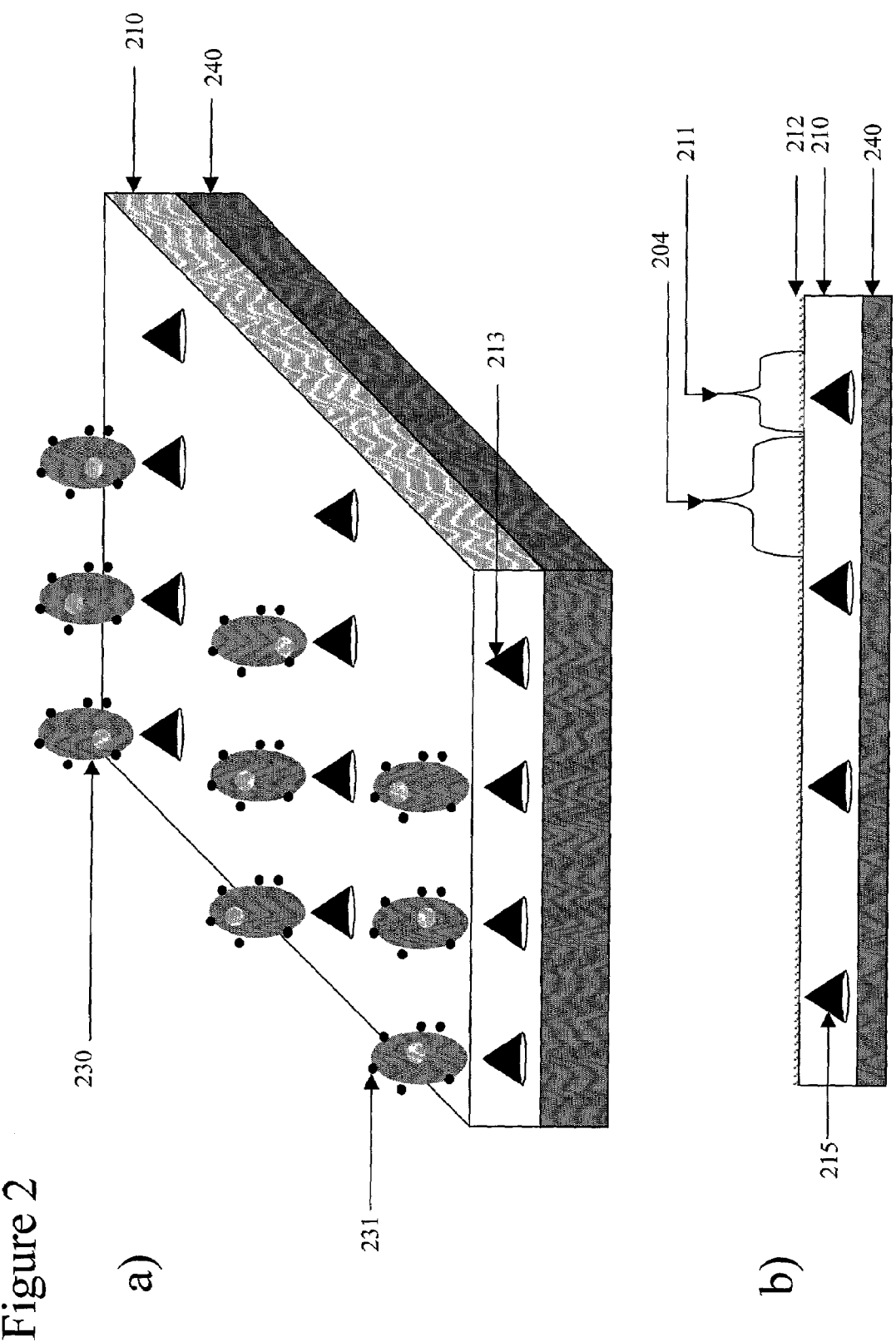
FIG. 2A) shows the substrate 210 in which is an embedded highly-magnetically-permeable material 213 which focuses the strength of an external magnet 240 to arrest cells 230 associated with magnetic material 231, in a perspective view. B) Illustrates in a cross-sectional view, highly-magnetically-permeable metallic horns 215 embedded in the substrate 210 focusing a the strength of an external magnet 240 to define a magnetic receptacle 211. The substrate may be treated to facilitate beading of cell-containing fluid 212. Area 204 shows an area outside of the magnetic receptacle which is not sufficiently magnetically attractive to immobilize cells associated with magnetic material.

The "substrate" as referred to herein, is any preferably substantially flat surface upon which magnetic receptacles and ultimately cells associated with magnetic material are immobilized and/or arrayed in a uniform pattern. FIGS. 1A and 2A. Preferably, the substrate is made of any material such as glass, co-polymer or polymer, most preferably urethanes, rubber, molded plastic, polymethylmethacrylate (PMMA), polycarbonate, polytetrafluoroethylene (TEFLON™), polyvinylchloride (PVC), polydimethylsiloxane (PDMS), polysulfone, and the like. Such substrates are readily manufactured from fabricated masters, using well known molding techniques, such as injection molding, embossing or stamping, or by polymerizing the polymeric precursor material within a mold. Standard soft lithography techniques may also be used to fabricate a substrate. See Love, et al., MRS BULLETIN, pp. 523-527 (July 2001) "Fabrication of Three-Dimensional Microfluidic Systems by Soft Lithography", Delamarche et al,: JOURNAL OF AMERICAN CHEMICAL SOCIETY, Vol. 120, pp. 500-508 (1998), Delamarche et al,: SCIENCE, Vol. 276, pp. 779-781 (May 1997), Quake et al., SCIENCE, Vol. 290, pp. 1536-1540 (Nov. 24, 2000), U.S. Pat. 6,090,251, all of which are hereby incorporated by reference for purposes of techniques for soft lithography and microfabrication. Such substrate materials are preferred for their ease of manufacture, low cost and disposability, as well as their general inertness to most extreme reaction conditions. These materials may include treated surfaces, such as, derivatized or coated surfaces, to enhance their utility in the fluidic, preferably microfluidic system, e.g., provide enhanced fluid direction, e.g., as described in U.S. Pat. No. 6,238,538, and which is incorporated herein by reference in its entirety for all purposes. Magnetic receptacles are disposed in predetermined locations on the substrate. FIG. 1B and FIG. 2B.

"Magnetic receptacle", as defined herein, refers to an area on the substrate capable of attracting, trapping, securing, or binding and thereby controlling the location of and preferably immobilizing a cell or small number of cells associated with magnetic material. FIGS. 1A, 1B and 2A, 2B. The magnetic receptacle has the ability to differentially attract, trap, secure and bind a cell or group of cells associated with magnetic material with respect to the non-attractive surrounding areas of the substrate. The shape of a magnetic receptacle may vary. For example, a magnetic receptacle may be substantially flat, or may have an indentation or concave area that may further serve to facilitate immobilization of individual or small numbers of cells associated with magnetic material. The magnetic receptacle is defined by a localized magnetic field gradient such that it is powerful enough to attract, bind, trap and thereby immobilize any desired number of cells associated with magnetic particles, yet weak enough to allow distinct non-attractive areas between receptacles. The invention is envisaged to have a substrate containing one or more magnetic receptacles. It is preferred, in some embodiments to focus the magnetic field gradient to capture a number of cells, such as one to one thousand, one to one hundred, one to ten and most preferably about one to about five cells.

A "discrete pattern" as defined herein refers to the immobilization of magnetically associated cells into and/or onto magnetic receptacles disposed in two dimensional arrays on the substrate. The magnetic receptacles may be arranged in any pattern so long as they immobilize magnetically associated cells at predefined locations such that the immobilized cells can be further experimentally manipulated. This characteristic would be beneficial, for example, if robotic high-throughput assays are performed where a machine repeatedly delivers a test compound or other analyte to a specific pre-programmed location. For example, a heterogeneous population of cells, such as hybridoma, may be immobilized into discrete magnetic receptacles and simultaneously tested with a specific antigen for antibody production using high-throughput techniques, by delivering the same antigen to each discrete cell or group of cells at each magnetic receptacle. Cells testing positive for production of the desired antibody may then be easily isolated from discrete locations on the substrate, using a cell isolation device. Alternatively, a homogeneous population of magnetically associated cells may be immobilized at predefined discrete locations such that the immobilized cells can be further experimentally manipulated by performing different manipulations or delivering a different test compound to each discrete cell or group of cells at each magnetic receptacle. For example, each cell or group of cells immobilized at a given magnetic receptacle may then be differentially mechanically or chemically manipulated and/or tested for a functional, physiological and/or phenotypic response to subset of a range of drug candidates or other test compounds, with respect to, a cell or group of cells immobilized at a different magnetic receptacle.

Devices of the invention preferably fits in the footprint of an industry standard microtiter plate. As such, the devices of the invention preferably has the same outer dimensions and overall size of an industry standard microtiter plate. Additionally, when the substrate comprises a discrete pattern of magnetic receptacles, the magnetic receptacles may have the same periodicity of an industry standard microtiter plate. The term "periodicity" used herein refers to the distance between respective vertical centerlines between adjacent magnetic receptacles or adjacent magnetic receptacles on/in the substrate of the device. The size and number of the plurality of magnetic receptacles can correspond to the footprint of standard 24-, 96-, 384-, 768- and 1536-well microtiter plates. For example, for a 96 well microtiter plate, the device of the invention may comprise 96 magnetic receptacles and therefore 96 experiments can be conducted. The present invention also contemplates any other number of magnetic receptacles disposed in any suitable configuration. By conforming to the exact dimension and specification of standard microtiter plates, embodiments of device would advantageously fit into existing infrastructure of fluid handling, storage, registration, and detection. Embodiments of the devices of the invention, therefore, may be conducive to high throughput screening as they may allow robotic fluid handling and automated detection and data analysis.

In one embodiment of this aspect of the invention shown in FIG. 1A, a magnetic receptacle derives its localized magnetic field gradient strength from one or more permanent magnets 5 embedded within the substrate, either partially or completely, or at a surface of the substrate 10, which act to place a localized magnetic field gradient at a given point or points along the substrate. One or more permanent magnets embedded at one or more locations in a substrate results in one or more magnetic receptacles, respectively. Permanent magnets of rare earth metals such as samarium cobalt may be used. Mixtures of rare earth metals may also be used. Preferably, neodymium iron boron is used. In this aspect of the invention the device does not require, yet still may employ the use of an external magnetic field. The "external magnetic field" as defined herein contemplates the use of electro- and permanent magnets 40.

This embodiment further contemplates the use of "horns" 19 fabricated from a permanent magnet. FIG. 1B. Permanent magnetic horns are permanent magnets of rare earth metals such as samarium cobalt and neodymium iron boron, fabricated into small shapes. The device may have only one horn giving rise to a single magnetic receptacle or multiple horns may be embedded at regular distances i.e., in a two-dimensional array with a periodicity of magnetic receptacles matching standard microtiter plates, such as a 96-, 384- and 1536-well microtiter plates, within the surface of the substrate 10. Horns are envisioned to direct a localized magnetic field gradient in a direction substantially perpendicular to the flow of cells over the substrate 10 or perpendicular to the surface of the substrate 10. The localized magnetic field gradient is strongest at the tip of the horn, where the permanent magnet's flux is focused. Preferably, the horns 19 will have a conical shape with a tip diameter of about the size of the diameter of the target cell. The invention envisages a tip diameter of about 10 to about 100 microns, most preferably about 15 to about 30 microns and being embedded in the substrate such that the tip of the cone-shaped horn is above, below or coplanar with the surface of the substrate 10.

Figure 3:
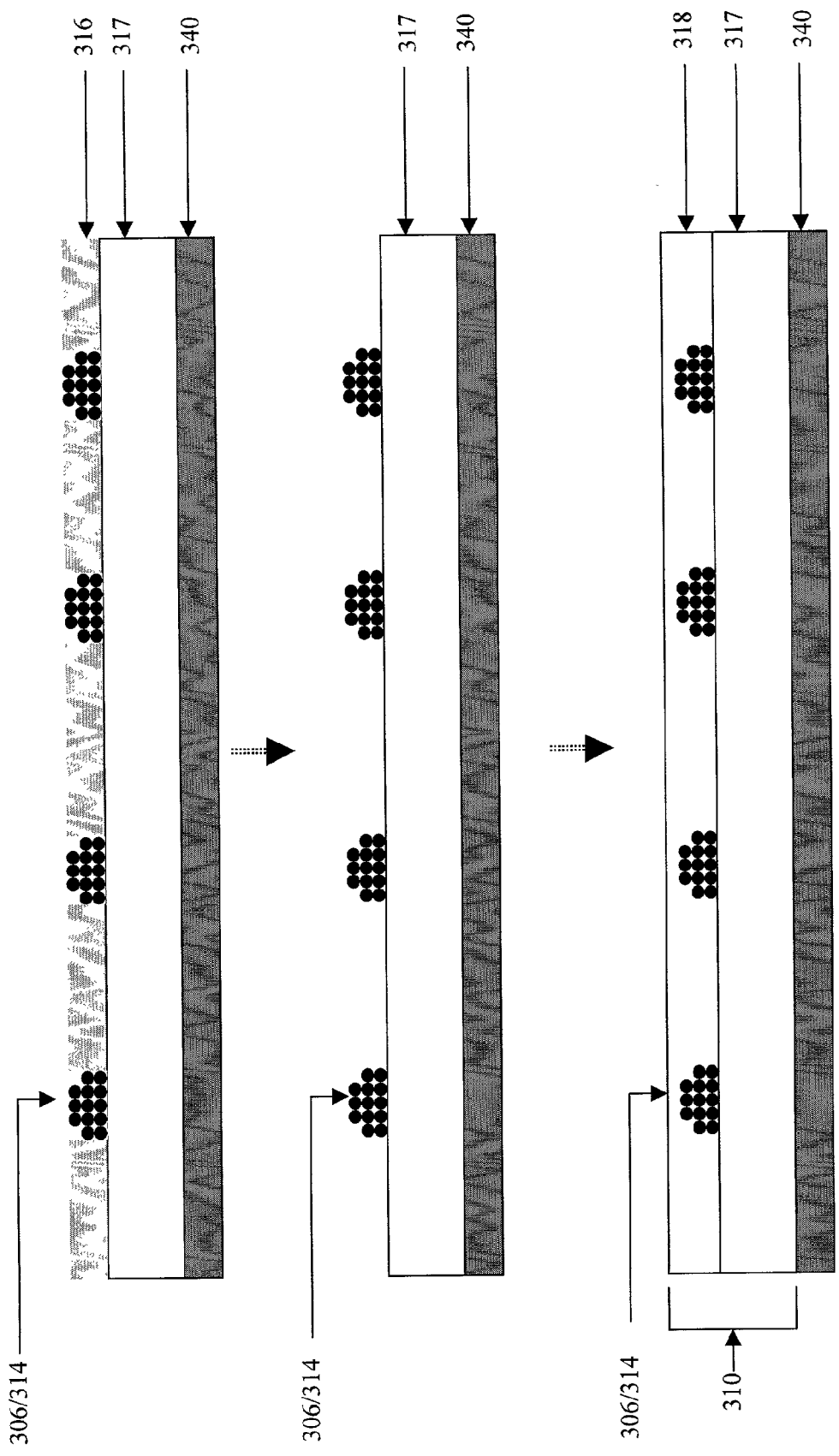
FIG. 3 illustrates in a cross-sectional view, how soft lithography may be used to pattern and array permanent magnets 306 or highly-magnetically-permeable metallic material 314 to focus an external magnetic field. The technique lays a membrane 316 having an array of micro-through holes over a solid substrate 317. Permanent magnet or highly-magnetically-permeable metal filings collect in the micro through-holes of the membrane 317. The membrane 316 is then removed leaving the permanent magnet 306 or highly-magnetically-permeable metallic filings 314 ordered in a patterned array on the solid substrate 317. A surface 318 is then cast and hardened over the array, resulting in an array of permanent magnet 306 or fixed highly-magnetically-permeable metal filings 314 within or at a surface of the substrate 310.

In a further embodiment of this aspect, soft lithography is used to deposit and/or array permanent magnetic material, i.e. filings 306 to focus an external magnetic field. FIG. 3. The technique lays a membrane 316 pattern, such as a photoresist, having an array of micro-through holes over a solid substrate 317. Permanent magnetic material collect in the micro through-holes of the membrane 306. The photoresist membrane 316 is then removed leaving the permanent magnetic material 306 ordered in a patterned array on the solid substrate 317. A surface 318 is then cast and hardened over the array resulting in an array of fixed permanent magnetic material within or at a surface of the substrate 310.

Alternatively, substrates having permanent magnetic material embedded therein can be manufactured by methods currently used in the manufacture of computer chips. In such a method, the substrate is first coated with a permanent magnetic material by a vapor deposition technique, such as vacuum evaporation or sputtering. Such a technique provides a layer of magnetic metal. A layer of photosensitive polymer, or photoresist, is then applied to the coated surface of the substrate and exposed to a pattern of ultraviolet light corresponding to the desired pattern of the magnetic receptacles on the substrate (or a negative image thereof, depending upon the photoresist employed). The photoresist is then developed to render undesired portions of the magnetic metal coating susceptible to removal by etching, such as wet chemical etching or reactive ion etching.

Such lithographic methods may be employed to produce a selected pattern of permanent magnetic metallization on a substrate. These lithographic techniques can be substantially cheaper than the use of electroplating or electroforming.

Alternatively, these method may be employed to deposit permanent magnetic material 306 in only a single location, resulting in a single magnetic receptacle.

In another embodiment of this aspect of the invention shown in FIG. 2A, a localized magnetic field gradient strength defining the magnetic receptacle is derived from highly-magnetically-permeable material 213 embedded within the substrate, either partially or completely, or at a surface of the substrate 210, which acts to create a localized magnetic field gradient at a given point. The device may have highly-magnetically-permeable material embedded at one or more locations in a substrate such that there are one or more magnetic receptacles, respectively.

The "external magnetic field" as defined herein contemplates the use of electro- and permanent magnets 240. Permanent external magnets of rare earth metals such as samarium cobalt may be used. Preferably, neodymium iron boron is used. External magnetic fields are focused by highly-magnetically-permeable material 213 to provide a focused localized magnetic field gradient.

A suitable "highly-magnetically-permeable material" 213 is characterized by having a high relative magnetic permeability ($\mu_r$) which is the permeability of the material ($\mu$) relative to the magnetic permeability of free space ($\mu_o$) as generally defined by the equation $\mu_r=\mu/\mu_o$. "Highly-magnetically-permeable material" would typically be a ferromagnetic metal. Examples of these, including their typical $\mu_r$ values, are: cobalt ($\mu_r=250$), soft iron ($\mu_r=5000$), silicon iron ($\mu_r=7000$). The highly-magnetically-permeable material 213 nickel ($\mu_r=600$) is preferred. Saidiku, Elements of Electromagnetics, Saunders College Publishing Ft. Worth, 1989. Chapter 8, pp. 322-386, herein incorporated by reference in its entirety for purposes of calculating magnetic permeability and attraction. Highly-magnetically-permeable material focuses the magnetic field at a given point, creating a localized magnetic field gradient which defines the magnetic receptacle.

Highly-magnetically-permeable material 213 is patterned above, below or on a surface of the substrate 210 in such a configuration to allow for immobilization of cell(s) in one or more magnetic receptacles or in discrete predetermined patterns. FIGS. 2A and 2B. Patterning of highly-magnetically-permeable material 213 to locally focus the external magnetic field can be accomplished by a variety of methods. The highly-magnetically-permeable material may be, but is not limited to the shape of a cone, inverted cone or pin.

In one embodiment of this aspect of the invention, the invention further contemplates the use of highly-magnetically-permeable horns 215 fabricated from a highly-magnetically-permeable material to pattern and focus an external magnetic field. FIG. 2B. The device may have only one highly-magnetically-permeable horn giving rise to a single magnetic receptacle or horns may be embedded in a irregular or regular pattern, preferably in a two-dimensional array with a periodicity of magnetic receptacles matching standard microtiter plates, such as a 96-, 384- and 1536-well microtiter plates, within the surface of the substrate 210. Horns are envisioned to direct a localized magnetic field gradient in a direction substantially perpendicular to the flow of cells over the substrate 210 or preferably substantially perpendicular to the surface of the substrate 210. The external magnetic field is preferably most focused at the tip of the horn, where the highly-magnetically-permeable material's magnetic flux is focused and a localized magnetic field gradient is created. Preferably, the horns 215 have a conical shape with a tip diameter of about 10 to 100 microns, most preferably about 15 to about 30 microns and are embedded in the substrate such that the tip of the cone-shaped horn is above, below or preferably coplanar with the surface of the substrate 210. It has been observed that sharper cones or horns produce larger localized magnetic field gradients, but will also reduce the area where there is essentially no lateral component to the field. Thus, for a given external magnetic field magnification, there will be a maximum cone angle that can be used without observing significant lateral forces. However, larger fields of view are desired to provide higher immobilized cell counts.

In a further embodiment of this aspect, soft lithography is used to deposit and/or array highly-magnetically-permeable permanent magnetic material, e.g. filings thereof 314 to focus an external magnetic field. FIG. 3. The technique lays a membrane 316 pattern, such as a photoresist, having an array of micro-through holes over a solid substrate 317. Highly-magnetically-permeable metal filings collect in the micro through-holes of the membrane 316. The membrane 316 is then removed leaving the highly-magnetically-permeable metallic filings 314 ordered in a patterned array on the solid substrate 317 the highly-magnetically-permeable material collect in the micro through-holes of the membrane. The photoresist membrane 316 is then removed leaving the highly-magnetically-permeable material 306 ordered in a patterned array on the solid substrate 317. A surface 318 is then cast and hardened over the array resulting in an array of fixed the highly-magnetically-permeable material within or at a surface of the substrate 310.

Alternatively, substrates having highly-magnetically-permeable material embedded therein can be manufactured by methods currently used in the manufacture of computer chips. In such a method, the substrate is first coated with a highly-magnetically-permeable material by a vapor deposition technique, such as vacuum evaporation or sputtering. Such a technique provides a layer of magnetic metal. A layer of photosensitive polymer, or photoresist, is then applied to the coated surface of the substrate and exposed to a pattern of ultraviolet light corresponding to the desired pattern of the magnetic receptacles on the substrate (or a negative image thereof, depending upon the photoresist employed). The photoresist is then developed to render undesired portions of the magnetic metal coating susceptible to removal by etching, such as wet chemical etching or reactive ion etching.

Such lithographic methods may be employed to produce a selected pattern of highly-magnetically-permeable metallization on a substrate. These lithographic techniques can be substantially cheaper than the use of electroplating or electroforming.

Alternatively, these method may be employed to deposit highly-magnetically-permeable material 314 in only a single location, resulting in a single magnetic receptacle.

In another embodiment of this aspect of the invention, a highly-magnetically-permeable material is selected such that its ability to generate a localized magnetic field gradient may be modulated by varying the temperature of the highly-magnetically-permeable material. This may be accomplished by employing a highly-magnetically-permeable material with a curie temperature close to the operating temperature of the device. Below its Curie temperature, highly-magnetically-permeable material will exhibit a high $\mu_r$, giving it the localized magnetic field gradient generating characteristics discussed above. Above its Curie temperature, the material loses its ferromagnetic character, and its $\mu_r$ approaches unity. One such material is gadolinium, whose Curie temperature is 19° C. Measurements of this are shown in Coey, et al., Nature, Vol. 401, 2 Sep. 1999, p36, herein incorporated by reference in its entirety. Localized magnetic field gradient-producing features fabricated from such a material, could be heated, removing the localized gradient and causing the release of the entrapped particles. Alloys of iron, nickel and cobalt, have been engineered to have a Curie point near room temperature. This phenomenon is used to make large-scale electromagnetic devices, for example as disclosed in U.S. Pat. No. 6,180,928, herein incorporated by reference in its entirety. At the micro-scale, tiny patterned areas of such material can be created in close proximity to tiny patterned heaters, which can be used to differentially switch magnetic receptacle attraction on and off on a highly localized basis.

The "localized magnetic field gradient" defines the strength of magnetic attraction at the site of the magnetic receptacle. This is defined one-dimensionally as H(dH/dx). Three dimensionally, this is defined by the equation $\nabla H^2$ or $2(H \cdot \nabla)H$. The strength of the localized magnetic field gradient used to arrest cells associated with magnetic material will depend on several factors including but not limited to the magnetizable material used to decorate target cells, including the type and amount of permanent magnet or highly-magnetically-permeable material used and the size, density and number of target cells. Preferably, the localized magnetic field gradient generates a force of about $5 \times 10^{-12}$ to about $5 \times 10^{-14}$, preferably $5 \times 10^{-13}$ Newtons, allowing arrest and stabilization of about one to about 20, and more preferably, one to about five cells.

The rate of capture can be adjusted by altering the localized magnetic field gradient strength. An approximate quantitative relationship between the net force (F) acting on a magnetic particle and the magnetic field gradient is given by the equation:

$$F = \frac{1}{2} \frac{\chi V_p}{\mu_0} \nabla(B^2)$$

where X is the difference between the magnetic susceptibility of the particle and the fluid, Vp is the volume of the particle. See Hatch et al., Journal of Magnetism and Magnetic Materials 225:262-271 (2001), which is herein incorporated by reference in its entirety. This expression is only an approximation since it ignores magnetic particle shape and particle interactions. Nevertheless, it does indicate that the force on a magnetic particle is directly proportional to the volume of that particle. As such, determination of the suitable magnetic field strength gradient is within the ordinary skill of one in the art.

One embodiment of this aspect of the invention is directed to a device having one or more permanent magnets 5 partially or completely embedded in or at a surface of the substrate 10, which capture single cells at each point defining a discrete magnetic receptacle 11. The strength of the localized magnetic field gradient depends in part on the size and inherent strength of the of permanent magnet in the substrate. FIGS. 1A and 1B.

Another embodiment of this aspect of the invention is directed to a device having one or more objects of highly-magnetically-permeable material 213 partially or completely embedded in the substrate 210 or at a surface of the substrate 210, which capture single cells at each point defining a discrete magnetic receptacle 211. The strength of the localized magnetic field gradient depends in part on the distance of external or electromagnets from the highly-magnetically-permeable material embedded in the substrate. The strength of the localized magnetic field gradient may further be weakened by positioning the highly-magnetically-permeable material 213 further below the surface of the substrate 210, or strengthened by positioning the highly-magnetically-permeable material 213 above the surface of the substrate. FIG. 2A and FIG. 2B.

The present invention's ability to immobilize and/or array cells allows the device to be used for filtration or enrichment of the cell-containing fluid for a particular cell-type. For example, this may be accomplished by negative selection of cells associated with magnetic material. In this method, a cellular subset of a cell containing fluid is purified by removing all other cell types from the fluid by using a bioaffinity ligand that is specific for all cell types other than the desired cellular subset. An advantage of this technique is that members of the desired cellular subset are not directly contacted. In another example, a desired subset of cells is positively selected by immobilization and/or arraying on the substrate.

Magnetically associated cells may be released from their immobilized state on the substrate or in the micro-gaps. The invention contemplates but is not limited to releasing the magnetically associated cells from the substrate by 1) disassociating the cells from the magnetic material such that they are no longer magnetically movable, by 2) increasing sheer forces of the cell-containing fluid such that they exceed the attractive strength of the magnetic receptacle on the magnetically associated cell, by 3) decreasing the strength of the localized magnetic field gradient such that magnetically associated cells are no longer sufficiently attracted to the magnetic receptacle to remain immobilized thereto, or by a combination of these techniques.

One of ordinary skill in the art would recognize a myriad of mechanisms facilitating dissociation of cells associated with magnetic material from the magnetic material. The invention includes but is not limited to the following examples. Immobilized magnetically associated cells may be incubated over night resulting in down-regulation or turnover cell surface molecules to which bioaffinity ligands are bound. In another example, proteolytic enzymes are used to release immobilized magnetically associated cells by cleaving cell surface molecules to which bioaffinity ligands are bound. In yet another example, synthetic peptides, competitively binding sugars or other chemicals ligates are introduced that out-compete cell surface molecules for binding to bioaffinity ligands. In yet another example, an antibody specific for the Fab' fragments of primary monoclonal antibodies on magnetic materials is added such that binding between the magnetic material and the cell's antigen is disrupted without changing the surface expression repertoire of the cell. In yet another example carbohydrate units on he Fc' part of antibodies acting as bioaffinity ligands mediate binding to and coating of magnetic particles. Sorbitol disrupts this binding and can be added to remove the magnetic material following cell immobilization. In yet a further example, lowering the pH of the cell containing liquid allows for the disassociation of magnetic particles from the cells. In yet another example, the bioaffinity ligand and ligate are complementary nucleotide linkers which may be cleaved upon exposure to DNase to disassociate magnetic material from immobilized cells.

One of ordinary skill in the art would recognize a myriad of way to increasing sheer forces of the cell-containing fluid such that they exceed the attractive strength of the magnetic receptacle on the magnetically associated cell. The invention includes but is not limited to the following examples. The flow rate of the cell containing fluid in the fluidic interface may be increased such that sheer forces exceed the attractive strength of the magnetic receptacle on the magnetically associated cell. Additionally, the speed of cells circulating over the magnetic receptacles may be increased such that sheer forces exceed the attractive strength of the magnetic receptacle on the magnetically associated cell. In another example additional fluid may be pippetted over the surface of the substrate to dislodge immobilized cells. In yet another example the device may be gently shaken to dislodge immobilized cells. In yet another example, and as described below, centrifugal force may be used to dislodge cells immobilized on the surface of the substrate.

One of ordinary skill in the art would recognize a myriad of ways to decrease the strength of the localized magnetic field gradient such that magnetically associated cells are no longer sufficiently attracted to the magnetic receptacle to remain immobilized thereto. The invention includes but is not limited to the following examples. Increasing the distance between the external magnetic field and the highly magnetically permeable material will decrease the strength of the localized magnetic field gradient. In another example, the temperature of the highly magnetically permeable material is increased above its Curie temperature. Above its Curie temperature, the material loses its ferromagnetic character, and its ability to generate a magnetic gradient.

Figure 4:
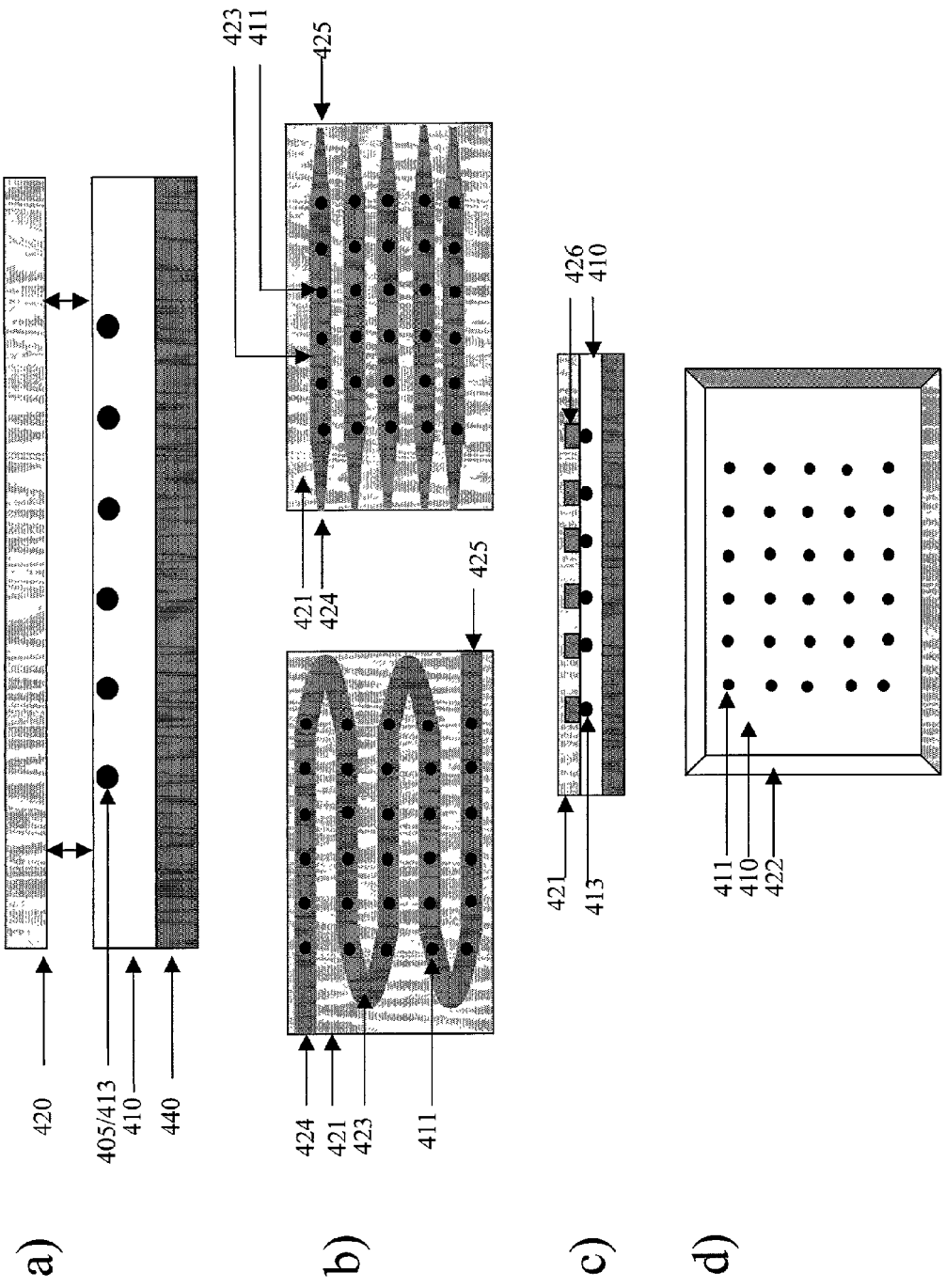
FIG. 4A) illustrates in a cross-sectional view, the removable cell delivery device 420 and the substrate 410 in which is embedded permanent magnets 405 or highly-magnetically-permeable metallic material 413 to be exposed to an external magnet 440. B) Shows in a perspective view, alternate fluidic channel 423 arrangements fabricated into a fluidic interface 421. The figure illustrates how when the fluidic interface 421 is mated to the substrate 410, the channels overlay the magnetic receptacles 411. C) Illustrates in a cross-sectional view, that the channels 423 are open grooves 426 that form enclosed channels 423 upon interface with the substrate 410. There is an in-port 424 and an out-port 425 for introducing and removing cell-containing fluid. D) Illustrates in a perspective view, the cell panning embodiment of the cell delivery 422 device mated to the substrate 410.

One aspect of the present invention contemplates the use of a cell delivery device. The "cell delivery device" 420 as used herein to refer to any member, apparatus or device that delivers cells to the substrate 410 upon which they are to be immobilized and/or arrayed. FIG. 4. The cell delivery device 420 flows, circulates, or delivers or otherwise causes cells and/or a cell-containing fluid to come into contact with the substrate 410 having one or more magnetic receptacles 411 disposed thereon. The invention contemplates, but is not limited to a cell delivery device utilizing a fluidic or microfluidic interface 421. FIG. 4B. The invention further contemplates, but is not limited to a cell delivery device capable of cell panning 422. FIG. 4D. Once cells have been immobilized and/or arrayed on the substrate, the cell delivery device 420 may be removed such that immobilized and/or arrayed cells are then accessible for experimentation, manipulation or further isolation.

In one embodiment of this aspect of the invention a fluidic device 421 is used as a cell delivery device 420. In this embodiment the channel 423 diameter and flow rate of the cell-containing fluid also affect the strength of the localized magnetic field gradient necessary to capture individual or small numbers of cells at magnetic a receptacle 411 (FIG. 4B).

In this embodiment, a removable cell delivery device 420 includes a fluidic interface 421 having one or more channels 423 capable of delivering a flow of cell-containing liquid to the substrate 410 on which one or more magnetic receptacles 411 are disposed. FIG. 4B.

A "fluidic" or "microfluidic interface" as described herein refers to a planar surface 421 into which channels 423 are fabricated. For examples please see U.S. Pat. No. 6,048,498, which is hereby incorporated by reference in its entirety. Preferably, the fluidic interface surface 421 is made of any material such as glass, co-polymer or polymer, most preferably urethanes, rubber, molded plastic polymethylmethacrylate (PMMA), polycarbonate, polytetrafluoroethylene (TEFLON™), polyvinylchloride (PVC), polydimethylsiloxane (PDMS), polysulfone, and the like. Such channeled planar surfaces are readily manufactured from fabricated masters, using well known molding techniques, such as injection molding, embossing or stamping, or by polymerizing a polymeric precursor material within the mold. Soft lithography techniques known in the art may also be used. See Love, et al., MRS BULLETIN, pp. 523-527 (July 2001) "Fabrication of Three-Dimensional Microfluidic Systems by Soft Lithography", Delamarche et al,: JOURNAL OF AMERICAN CHEMICAL SOCIETY, Vol. 120, pp. 500-508 (1998), Delamarche et al,: SCIENCE, Vol. 276, pp. 779-781 (May 1997), Quake et al., SCIENCE, Vol. 290, pp. 1536-1540 (Nov. 24, 2000), U.S. Pat. No. 6,090,251, all of which are hereby incorporated by reference. Such materials are preferred for their ease of manufacture, low cost and disposability, as well as their general inertness to most extreme reaction conditions.

Channels 423 are fabricated open grooves 426 in the bottom of the planar surface of the fluidic device 421. FIG. 4B. Typically a planar bottom surface is fabricated by known techniques, e.g., photolithography, wet chemical etching, laser ablation, air abrasion techniques, injection molding, or embossing. When the channeled planar surface of the fluidic device 421 is mated to the substrate 410 upon which one or more magnetic receptacles 411 are disposed, the open grooves 426 are sealed by the substrate and define channels 423 closed on all sides, which are capable of flowing liquid by either capillary action, positive pressure or vacuum force. The mating of the fluidic interface 421, which has a plurality of grooves with the substrate creates a network of channels 423 through which the cell-containing fluid flows over the substrate 410 upon which one or more magnetic receptacles 411 are disposed. Once cells associated with magnetic material 430 have been immobilized and/or arrayed on the substrate 410, the cell delivery device 420 having the fluidic interface 21 may be removed to further manipulate, isolate or transfer cells.

The diameter of the channels 423 of the fluidic interface 421 should be large enough to prevent clogging of the channel, preferably at least about three times the diameter of a cell, e.g. 100 µm×100 µm. The diameter of the channel 423 affects the localized magnetic strength required by the magnetic receptacle 411 to arrest cells. Additionally, a larger diameter requires more pressure to force the cell-containing fluid through the channels. Thus, the preferred channel 423 diameter depends upon the size of the cells to be captured, the force used to move the cell containing fluid through the channels and the size and strength of the localized magnetic field gradient of the magnetic receptacle 411. For a review of microfluidics see the following Love, et al., MRS BULLETIN, pp.523-527 (July 2001) "Fabrication of Three-Dimensional Microfluidic Systems by Soft Lithography", Delamarche et al,: JOURNAL OF AMERICAN CHEMICAL SOCIETY, Vol. 120, pp. 500-508 (1998), Delamarche et al,: SCIENCE, Vol.276, pp.779-781 (May 1997), Quake et al., SCIENCE, Vol. 290, pp. 1536-1540 (Nov. 24, 2000), U.S. Pat. No. 6,090,251, all of which are hereby incorporated by reference.

The cell delivery device 420 having a fluidic interface 421 has an inlet port 424 into the housing and an outlet port 425 to allow cell-containing fluid to enter, flow through, and exit a channel. FIG. 4C shows two potential variations of fluidic interfaces envisioned in the invention. Removing the removable cell delivery device 420 exposes the substrate 410 which has an array of magnetic receptacles 411 disposed thereon. The magnetic receptacles 411 are positioned on the substrate 410 such that a liquid sample will flow through the fluidic interface and past the magnetic receptacles 411. Magnetic receptacles 411 exert a magnetic attraction in a direction substantially perpendicular to the direction of fluid flow. Preferably, the magnetic receptacles 411 are disposed in a two-dimensional array with a periodicity of magnetic receptacles matching standard microtiter plates used in the industry such as the 96-, 384-, and 1536-well plates.

In another embodiment of this aspect of the invention, the removable cell delivery device 420 pans cells over the substrate 410 as shown by 422. FIG. 4D. Removing the removable cell delivery device 420 exposes the substrate 410 which has an array of magnetic receptacles 411 thereon. In this embodiment, the cell delivery device 420 has a flexible perimeter 422 which is mated to the edges of the substrate 410 such that the flow of cell-containing fluid is restricted to an area of the substrate 410 upon which magnetic receptacles 411 are disposed. The cell-containing fluid may be introduced to the cell delivery device in several ways including but not limited to a pipette or by otherwise pouring the cell-containing fluid on the substrate such that the total volume of the cell-containing fluid does not exceed the capacity of the cell delivery device mated to the substrate. Exceeding the capacity of this embodiment of the cell delivery device mated to the substrate will result in cell-containing fluid spilling out of the apparatus. Preferably, the cell delivery device 420 is made of glass, urethanes, rubber, molded plastic a flexible plastic or another flexible co-polymer or polymer, such as polymethylmethacrylate (PMMA), polycarbonate, polytetrafluoroethylene (TEFLON™), polyvinylchloride (PVC), polydimethylsiloxane (PDMS), polysulfone, and the like. Such devices are readily manufactured from fabricated masters, using well known molding techniques, such as injection molding, embossing or stamping, or by polymerizing the polymeric precursor material within the mold. Such materials are preferred for their ease of manufacture, low cost and disposability, as well as their general inertness to most extreme reaction conditions.

In this embodiment, cell containing fluid is added to the cell delivery device 422 mated to the substrate 410 and continuously rotated so as to circulate the fluid over the magnetic receptacles 411. The circulation of fluid uniformly distributes cells associated with magnetic material 430 over the magnetic receptacles 411. Following delivery of the cell-containing fluid, cell-free fluid may be circulated over the magnetic receptacles 411 to wash through any unbound cells.

In this embodiment of the cell delivery device 422, the strength and vigor of fluid circulation as determined by speed of device rotation, will also affect the strength of the localized magnetic field gradients necessary to capture individual or small numbers of cells at magnetic receptacles 411. Generally, an increase in the strength and vigor of circulation as well as an increase in fluidic flow result in increased shear forces between cells 430 and magnetic receptacles 411, requiring increased localized magnetic strength to keep a cell magnetically immobilized.

Figure 5:
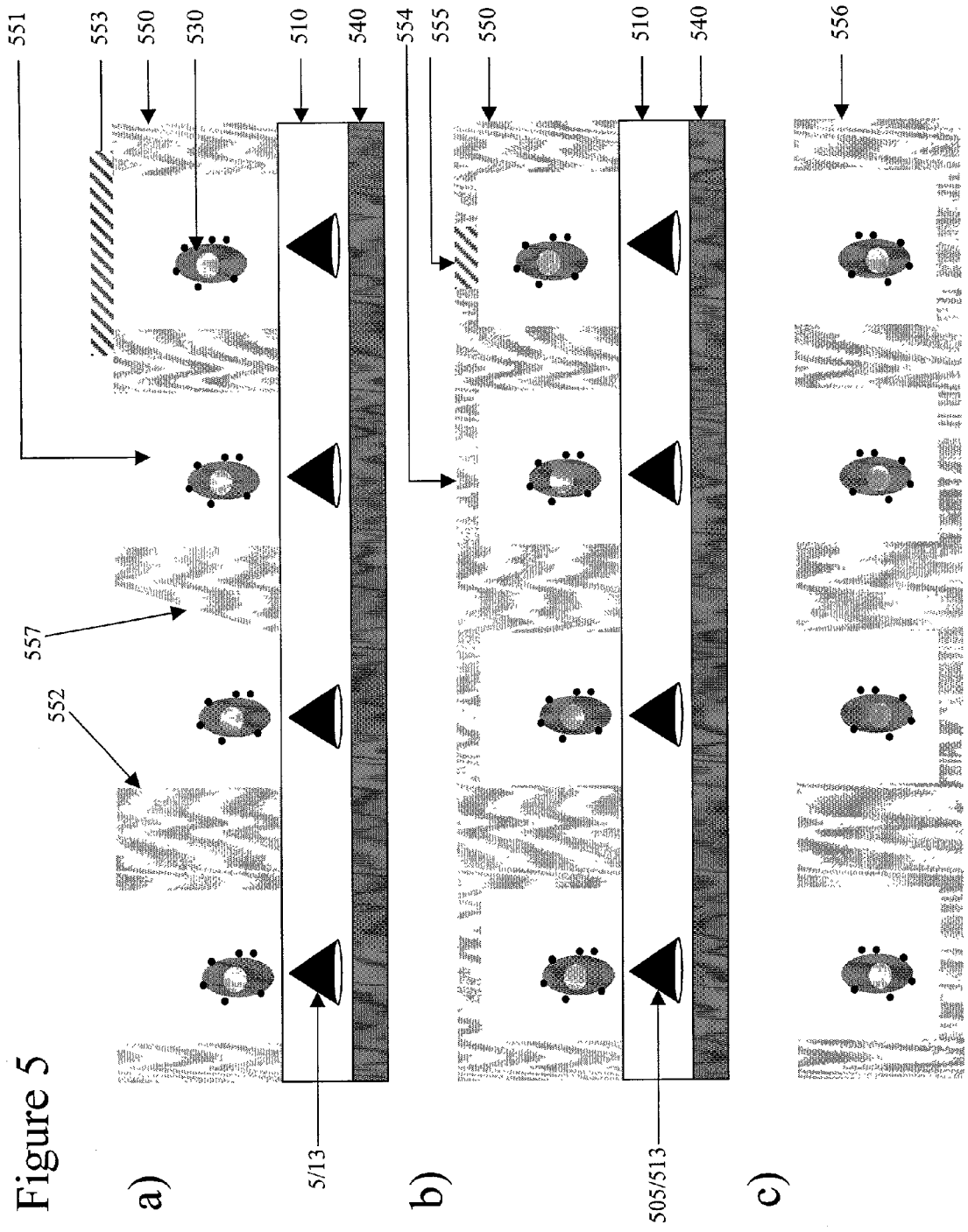
FIG. 5 shows various embodiments of the cell isolation device in cross-section. a) Illustrates the cell isolation device 550.

Yet another aspect of the invention allows for the further isolation and/or clonal expansion and feeding of cells immobilized on the substrate. This aspect of the invention utilizes a cell isolation device. FIG. 5A. Once cells are immobilized and/or arrayed on the substrate the cell delivery device 520 is removed and the substrate is interfaced with a cell isolation device. A cell isolation device will preferably have the same periodicity as the magnetic receptacles 511 disposed on the substrate 510. The cell isolation device has a membrane which inhibits fluid communication between the immobilized and/or arrayed cells, in each magnetic receptacle. Individual cells can then be assayed and maintained in the areas defined by the membrane in the absence of a magnetic field. Preferably, the membrane 550 is of a specified thickness and periodicity such that once it is in place on the substrate 510, it will form one or more wells to isolate each cell or small number of cells to provide adequate volume for any desired experiment or cellular manipulation, such as potential clonal expansion. The membrane 550 is further intended to provide for any number of wells, but preferably, about 385 and most preferably about 1536 wells. Larger well volumes can be achieved by extending the depth of the membrane well without compromising the aspect ratio. Wells may be of any shape, but circular or square shapes are preferred as these shapes are commonly used in the industry.

Preferably, the material used for the manufacture of the cell isolation device 550 is any rigid or flexible material such as glass, urethanes, rubber, molded plastic, co-polymer or polymer, more preferably urethanes, rubber, molded plastic, polymethylmethacrylate (PMMA), polycarbonate, polytetrafluoroethylene (TEFLON™), polyvinylchloride (PVC), polydimethylsiloxane (PDMS), polysulfone, and the like, and most preferably PDMS. Such membranes are readily manufactured from fabricated masters, using well known molding techniques, such as injection molding, embossing or stamping, or by polymerizing the polymeric precursor material within the mold. Such materials are preferred for their ease of manufacture, low cost and disposability, as well as their general inertness to most extreme reaction conditions.

In a preferred embodiment of this aspect of the invention, the cell isolation device 550 includes a membrane having one or more micro through-holes 551 with a periodicity matching the position of magnetic receptacles 511 on the substrate 510. The interface between the cell isolation device 550, membrane having through-holes 551 and the substrate 510 on which cells are immobilized forms one or more discrete wells with a periodicity matching the pattern of magnetic receptacles 511 on the substrate 510.

In another embodiment, the membrane 550 has one or more through-hole walls 552 that are perpendicular to the substrate which forms the well floor, or canted relative to substrate 510. Canted wells 557 permit easier access by allowing for lateral movement when performing downstream experiments on cells in the wells, whereas straight walled wells provide a greater volume that may increase the time available for the detection assay. Furthermore, a canted well 557 design may create a more uniform interface with a small receptacle.

Yet another embodiment of this aspect of this invention further contemplates use of a cell isolation device 550 wherein the micro through-hole containing membrane may have an additional membrane 553 opposite the substrate 510, which restricts cell movement, yet permits exchange of media, thereby allowing the investigator to combine cell expansion and refeeding events. Cells will be retained in the well by a size-constraining membrane 553 or semi-permeable membrane, such as a dialysis membrane, nitrocellulose or perforated polydimethyl sialoxane (PDMS), for example. The initial flow-through of old medium can be drained either by positive pressure, vacuum, or gravity to capture liquid putatively containing substances secreted by the immobilized and/or arrayed target cell on a surface designed for sampling/detection e.g., nitrocellulose, glass, urethanes, rubber, molded plastic, PDMS. For example, the individually immobilized and/or arrayed target cells may heterogenous hybridoma cells and the secreted substance may be monoclonal antibodies.

In yet another embodiment of this aspect of this invention, the cell isolation device 550 includes a membrane having one or more inverted wells 554, rather than through-holes, with a periodicity matching the array of magnetic receptacles 511 on the substrate 510. FIG. 5B. The interface between the cell isolation device having a membrane with inverted wells 554 and the substrate 510 on which cells are immobilized seals the inverted well and completely separates cells into discrete chambers.

Another embodiment of this aspect of this invention, further contemplates a mechanism for transferring cells 530 from the substrate 510 to the cell isolation device 554. This mechanism for transferring cells from their magnetic receptacles 511 to the inverted membrane wells of the cell isolation device 554 is intended to function by use of centrifugal force. Cells immobilized on the substrate 510 can be spun into the larger membrane well 554 of the cell isolation device. The cell isolation device 554 and substrate 510 are inverted, and the substrate 510 removed. Removal of the inverted substrate 510 brings the cell isolation device 554 to right-side-up conformation resembling a membrane with one or more wells 556, similar to a microtiter plate, with a periodicity matching that of the magnetic receptacles 510 of the substrate 510. See FIG. 5C. Cells are thus transferred into the right-side up wells of the cell isolation device 556. Additional media may be added to the wells to permit growth and viability. The cell isolation device wells 554 maintain the same periodicity as the substrate, but can have wells 554 of greater diameter or deeper well volume.

In yet a further embodiment of this aspect of the invention, a cell isolation device 550 is contemplated, wherein the well-containing membrane may have a semi-permeable opening 555 opposite the substrate 510 of each inverted well 554 restricting cell movement, yet permitting exchange of media, and thereby allowing cell expansion and refeeding, for example. Cells are retained by a size constraint or semi-permeable membrane, such as a dialysis membrane, nitrocellulose or perforated polydimethyl sialoxane (PDMS), for example. The initial flow-through of old medium may be drained by positive pressure, vacuum, or gravity to capture liquid putatively containing antibody on a surface designed for sampling/detection, e.g., nitrocellulose, glass, urethanes, rubber, molded plastic, PDMS.

Figure 6:
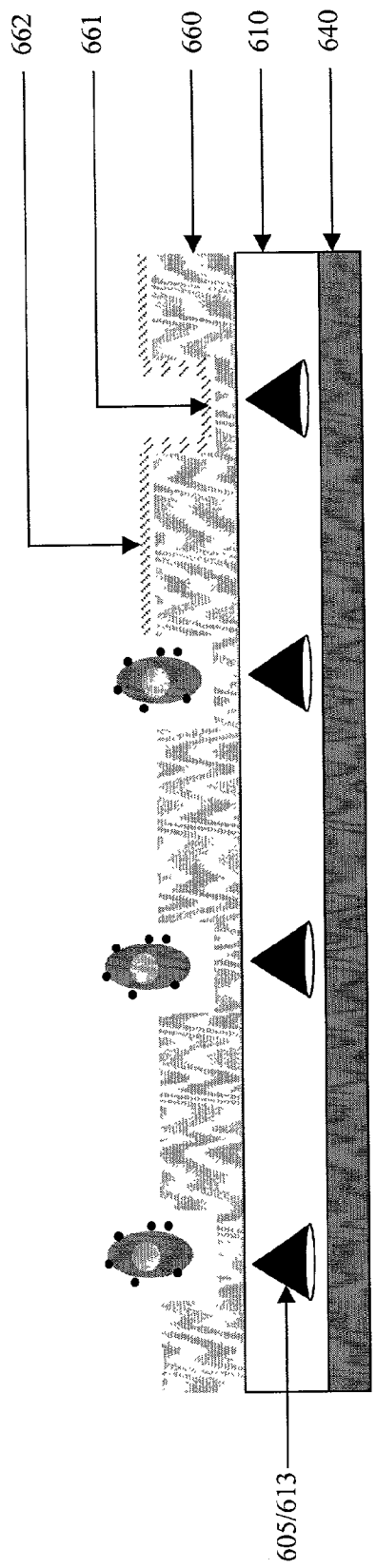
FIG. 6 shows in a cross-sectional view, a layer 660 having micro-gaps 661 which is laid over the substrate 610 upon which magnetic receptacles are disposed. The micro-gaps 661 are positioned over the permanent magnets 605 or highly-magnetically-permeable material 613 disposed in the substrate 610. Alternatively, the micro-gap 661 area and area adjacent to the micro-gap 662 may be treated to provide a hydrophobic environment.
Figure 7:
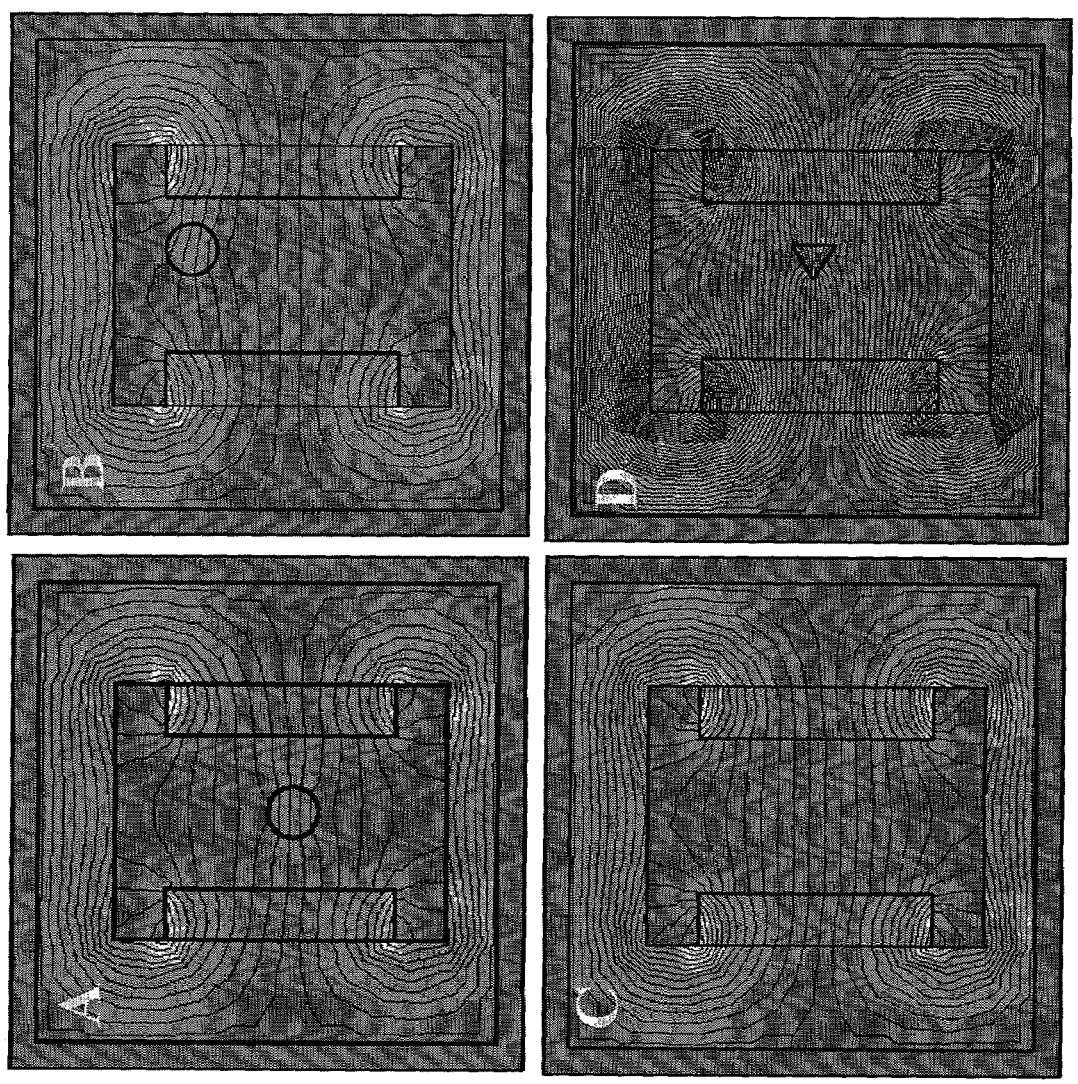
FIG. 7(A) shows a magnetic particle in a weak external magnetic field with very little magnetic field gradient. The magnetic particle will experience very little force. (B) shows the same magnetic particle in the same magnetic field as (A) in a position where there is a magnetic field gradient which increases with proximity to the magnetic pole. The particle experiences increasing magnetic force. (C) shows a stronger yet more uniform external magnetic field with little or no gradient in the center. (D) illustrates how "highly-magnetically-permeable material" having a high relative magnetic permeability ($\mu_r$) generates a localized magnetic field gradient in the uniform external magnetic field.

In yet a further embodiment of the present invention, a layer 660 having one or more micro-gaps 661 is laid over the substrate 610 upon which one or more magnetic receptacles 611 are disposed. FIG. 6. The micro-gaps 661 are positioned over the highly-magnetically-permeable material 613 embedded in the substrate 610. Alternatively, the micro-gaps 661 are positioned over the permanent magnetic material 613 embedded in the substrate 610. The size of the micro-gaps 661 depends on the size, shape and number of cells associated with magnetic material 630 to be captured in each micro-gap 661. The localized magnetic field gradient resulting from the highly-magnetically-permeable material 613 disposed in the substrates is adjusted such that the size of the magnetic receptacle 611 extends into the micro-gap 661. As such, the cells associated with magnetic material 630 are attracted thereto and trapped therein. Once cells have been immobilized and/or arrayed on the layer 660 into micro-gaps 661, the cell delivery device 620 may be removed such that immobilized and/or arrayed cells are then accessible for experimentation, manipulation or further isolation.

Preferably, the layer 660 with one or more micro-gaps 661 is made of any flexible or rigid material such as glass, urethanes, rubber, molded plastic, co-polymer or polymer, more preferably urethanes, rubber, molded plastic, polymethylmethacrylate (PMMA), polycarbonate, polytetrafluoroethylene (TEFLON™), polyvinylchloride (PVC), polydimethylsiloxane (PDMS), polysulfone, and the like. Such layers are readily manufactured from fabricated masters, using well known molding techniques, such as injection molding, embossing or stamping, or by polymerizing the polymeric precursor material within the mold. Such materials are preferred for their ease of manufacture, low cost and disposability, as well as their general inertness to most extreme reaction conditions.

One embodiment of this aspect of the invention contemplates, but is not limited to a cell delivery device utilizing a fluidic interface. Another embodiment further contemplates, but is not limited to a cell delivery device capable of cell panning. Accordingly, cells are delivered to the layer having micro-gaps by way of the same cell delivery devices, (i.e., cell panning device and fluidic interface) discussed above. The cell delivery device functions to deliver cells associated with magnetic material to the layer with micro-gaps in which they are to be immobilized and/or arrayed. The cell delivery device flows or circulates a cell containing fluid over the substrate having magnetic receptacles disposed thereon.

In another embodiment of this aspect of the invention, cells may be further isolated from the layer containing micro-gaps using a cell isolation device of the type included in the general description of the cell delivery device above. Once cells are captured in an ordered array on the layer with micro-gaps the cell delivery device is removed and the layer is mated to the cell isolation device. A cell isolation device will preferably have either micro through-holes or wells with the same periodicity as the micro-gaps in the layer and magnetic receptacles on the substrate. The cell isolation device membrane inhibits fluid communication between the immobilized and/or arrayed cells. Also, cell movement is restricted by the cell isolation device. Individual cells can then be assayed and maintained in the areas defined by the cell isolation device membrane in the absence of a magnetic field.

In yet a further embodiment of the present invention, all surfaces that come into contact with the cell containing fluid are treated to provide a more hydrophobic environment. These surfaces include the substrate, magnetic receptacle(s), cell delivery device for panning, cell delivery device with fluidic channels, cell isolation device, and/or the layer with micro-gaps. Hydrophobic surfaces would favor the beading of liquid containing cells in or on the magnetic receptacle and potentially facilitate holding the cells in place. Examples of some hydrophobic surface treatments which are known in the art to prevent protein and cell attachment include teflon, perfluoronated plastic, polyethylene glycol, ethylene oxide-terminated trichlorosilane, hydrophobic alkyltrichlorosilane, and the like.

In another embodiment of the invention wherein the cell-containing fluid is blood, plasma, or a solution containing blood products likely to cause coagulation such as platelets, the substrate, magnetic receptacle(s), cell delivery device for panning, cell delivery device with fluidic channels, cell isolation device, and/or the layer with micro-gaps are treated to inhibit coagulation and clot formation. The surface treatment favors the even flow and distribution of the cell-containing liquid over the magnetic receptacle(s). Examples of such anti-coagulant surface treatments which are known in the art to prevent coagulation and clot formation include heparin, heparin fragments, tissue-type plasminogen activator (tPA), urokinase (uPA), anti-thrombosis agents (such as Hirudan) and albumin. Also suitable are anti-coagulant agents which are antibodies, for example antibodies directed against platelet receptor GPIB and/or GPIB, against platelet receptor GPIIb/IIIa, and/or against von Willebrand Factor (vWF).

In yet another embodiment of the invention, antibody-coated magnetic particles 31 are initially deposited onto or into one or more magnetic receptacles, then cells flowing over the antibody-coupled magnetic particles remain bound to the receptacle by way of immuno-specific affinity. An antibody that is specific for a particular cell type may be employed.

The invention is contemplated to be used at any biologically viable temperature. Lowering the incubation temperature of the cells (e.g., from 37° C. to 18° C.) may slow the metabolic processes of the cells and the cell doubling time, thus extending the time for individual cell experimentation and manipulation.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

Several permanent neodymium iron boron magnets each with a strength of 12,000 Gauss, are embedded in a PDMS substrate. A magnetic bead-containing phosphate buffered saline (PBS) solution is introduced to a cell panning device mated to the substrate. 2 ml of magnetic beads in suspension (Spherotech™ 9 µm diameter beads at a density of $1\times10^6$ beads/µl suspension) are uniformly distributed by cell panning. The coupled substrate and cell delivery device are rotated for a period of 30 minutes at 0.5 RPM. The substrate with immobilized beads is washed with cell-free PBS. The local magnetic field gradient derived from each of the permanent magnets captures several thousand beads on the PDMS substrate above the embedded magnets, forming the desired array on the substrate.

Example 2

Several permanent neodymium iron boron magnets each with a strength of 12,000 Gauss, are embedded in the PDMS substrate. 1 ml Spherotech™ (1840 Industrial Dr., Suite 270 Libertyville, Ill. 60048-9467) 9 µm diameter magnetic beads at a density of $1\times10^6$ beads/µl suspension coated with the bioaffinity ligand streptavidin are pre-incubated with a biotinylated anti-mouse anti-syndecan antibody at a final antibody concentration of 50 µg/ml. The antibody conjugated beads are then washed to PBS remove unbound antibody. 1 ml hybridoma cells ($2\times10^5$/µl) in RPMI media are then incubated with 1 ml antibody conjugated Spherotech™ 9 µm diameter magnetic beads at a density of $1\times10^6$ beads/µl suspension 2 ml of the magnetic bead and cell containing RPMI media (Sigma; www.sigma-aldrich.com) is introduced to the cell panning device mated to the substrate. The coupled substrate and cell delivery device are rotated for a period of 3 hours at 3 RPM. The substrate with immobilized cells is washed with cell-free PBS. The external magnetic field derived from each of the permanent magnets captures several thousand cells on the PDMS substrate above the embedded magnets, forming the desired array on the substrate.

Example 3

Several localized magnetic field gradients are derived from several small permanent magnetic pins embedded in PDMS with their tips coplanar with the substrate. The permanently magnetic pins generate a several localized magnetic field gradients, each with an attractive force of about $5\times10^{-13}$ Newtons on cells associated with magnetic material passing over the substrate. 1 ml Spherotech™ 9 µm diameter magnetic beads at a density of $1\times10^6$ beads/µl suspension coated with the bioaffinity ligand streptavidin are pre-incubated with a biotinylated anti-mouse anti-syndecan antibody at a final antibody concentration of 50 µg/ml. The antibody conjugated beads are then washed to PBS remove unbound antibody. 1 ml hybridoma cells ($2\times10^5$/µl) in RPMI media are then incubated with 1 ml antibody conjugated Spherotech™ 9 µm diameter magnetic beads at a density of $1\times10^6$ beads/µl suspension 50 µl of the magnetic bead and cell containing RPMI media (Sigma) is introduced into the in-port of the cell delivery device's microfluidic interface as shown in FIG. 4B, which has a channel with a diameter of $100\times100$ µm when mated to the substrate. The immobilized cells are washed by introducing 50 µl of cell-free PBS into the microfluidic interface channel. The magnetic receptacle above the tip of each of the permanent magnetic pins arrest one to five cells at about a 1.0 µl/second minute flow rate in the 100×100 µm channel, forming the desired array on the substrate, forming the desired array on the substrate.

Example 4

The external neodymium iron boron magnet has a strength of 12,000 Gauss. Stainless steel highly-magnetically-permeable pins embedded in PDMS with their tips coplanar with the substrate create localized magnetic field gradients. 1 ml Spherotech™ 9 µm diameter magnetic beads at a density of $1 \times 10^6$ beads/µl suspension coated with the bioaffinity ligand streptavidin are pre-incubated with a biotinylated anti-mouse anti-syndecan antibody at a final antibody concentration of 50 µg/ml. The antibody conjugated beads are then washed to PBS remove unbound antibody. 1 ml hybridoma cells (at a concentration of $2 \times 10^5$/µl) in RPMI media are then incubated with 1 ml antibody conjugated Spherotech™ 9 µm diameter magnetic beads at a density of $1 \times 10^6$ beads/µl suspension 50 µl of the magnetic bead and cell containing RPMI media (Sigma) is introduced into the in-port of the cell delivery device's microfluidic interface as shown in FIG. 4B, which had channel with a diameter of 100×100 µm when mated to the substrate. The immobilized cells are washed by introducing 50 µl of cell-free PBS into the microfluidic interface channel. The magnetic receptacles above the tips of each of the highly-magnetically-permeable pins is able to arrest one to five cells at about a 1.0 µl/second minute flow rate in the 100×100 µm channel, forming the desired array on the substrate.

What is claimed is:

1. A device for arraying a plurality of cells into discrete and predetermined locations for further experimentation, said device comprising a substrate having an essentially flat surface, wherein a plurality of magnets are contained in said substrate, wherein said plurality of magnets are arrayed in said substrate such that each magnet defines a localized magnetic field gradient to define a magnetic area, wherein said magnetic area is situated on the surface of the substrate in a predetermined location discrete from other magnetic areas to provide a plurality of discrete magnetic areas, wherein the plurality of magnetic areas defined by said plurality of magnets are disposed in a two-dimensional array on the substrate, wherein said localized magnetic field gradient immobilize one to about five cells within said each of said plurality of magnetic areas, wherein said cells are associated with magnetic material at the time that said cells are immobilized within said plurality of magnetic areas.

2. The device of claim 1 wherein said cells are hybridoma cells.

3. The device of claim 1 wherein the substrate is fabricated from a material selected from the group consisting of glass, urethane, rubber, molded plastic, polymethylmethacrylate, polycarbonate, polytetrafluoroethylene, polyvinylchloride, polydimethylsiloxane, and polysulfone.

4. The device of claim 1 further comprising a layer on top of said substrate wherein said layer has micro-gaps positioned over said magnetic areas.

5. The device of claim 1 further comprising a cell isolation device, wherein said cell isolation device comprises a membrane containing a plurality of wells that match the plurality of the magnetic areas, such that when said cell isolation device is placed on said substrate, said cell isolation device is capable of isolating said one to about 5 cells immobilized in one of said plurality of magnetic areas from other of said cells immobilized in said other of said plurality of magnetic areas arrayed within the cell isolation device.

6. The device of claim 5, wherein the wells of the cell isolation device are micro through-holes, wherein the micro through-holes are defined by inner walls of the membrane.

7. The device of claim 6, wherein the device further comprises a semi-permeable membrane opposite the substrate, wherein said semi-permeable membrane restricts cell movement between wells and is permeable to fluid.

8. The device of claim 7 wherein at least one of the walls of the micro through-holes are canted or perpendicular to the substrate.

9. The device of claim 5, wherein said plurality of magnetic areas further comprises immobilized cells, such that when the cell isolation device is placed on said substrate, said cells are capable of being transferred from said plurality of magnetic areas to said cell isolation device, and when the substrate is removed, the cells remain in the cell isolation device.

10. The device of claim 9 wherein said cells are capable of being transferred from said plurality of magnetic areas to said cell isolation device by centrifugal force.

11. The device of claim 1 wherein the substrate is coated with a hydrophobic agent.

12. The device of claim 11 wherein the hydrophobic agent is selected from the group consisting of teflon, perfluoronated plastic, polyethylene glycol, ethylene oxide-terminated trichlorosilane, and hydrophobic alkyltrichlorosilane.

13. The device of claim 1 wherein the substrate is coated with an anti-coagulant.

14. The device of claim 13 wherein the anti-coagulant is selected from the group consisting of heparin, heparin fragments, tissue-type plasminogen activator (tPA), urokinase (uPA), Hirudan, albumin, anti-platelet receptor GPIB antibodies, anti-platelet receptor GPIIb/IIIa antibodies, and anti-von Willebrand Factor (vWF) antibodies.

15. The device of claim 1 wherein at least one of the magnets is a permanent magnet.

16. The device of claim 1 wherein at least one of the magnets is made of highly-magnetically-permeable material.

* * * * *